United States Patent
Kim et al.

(10) Patent No.: US 7,816,021 B2
(45) Date of Patent: Oct. 19, 2010

(54) CARBAZOLE-BASED COMPOUND AND ORGANIC LIGHT-EMITTING DEVICE INCLUDING ORGANIC LAYER INCLUDING THE CARBAZOLE-BASED COMPOUND

(75) Inventors: Young-Kook Kim, Suwon-si (KR); Seok-Hwan Hwang, Suwon-si (KR); Yoon-Hyun Kwak, Suwon-si (KR)

(73) Assignee: Samsung Mobile Display Co., Ltd., Suwon-si (KR)

( * ) Notice: Subject to any disclaimer, the term of this patent is extended or adjusted under 35 U.S.C. 154(b) by 422 days.

(21) Appl. No.: 11/926,364

(22) Filed: Oct. 29, 2007

(65) Prior Publication Data

US 2008/0174237 A1   Jul. 24, 2008

(30) Foreign Application Priority Data

Jan. 18, 2007   (KR) ...................... 10-2007-0005817

(51) Int. Cl.
  H01L 51/54 (2006.01)
  C07D 403/14 (2006.01)
  H01J 1/62 (2006.01)

(52) U.S. Cl. .................. 428/690; 428/917; 548/440; 548/446; 313/504; 313/506

(58) Field of Classification Search .................. None
See application file for complete search history.

(56) References Cited

U.S. PATENT DOCUMENTS 6,465,115 B2   10/2002   Shi et al.
6,596,415 B2   7/2003   Shi et al.

FOREIGN PATENT DOCUMENTS

JP   11-329734   11/1999
KR   2007-9456   1/2007

OTHER PUBLICATIONS

Adachi et al. "Endothermic Energy Transfer: A Mechanism for Generating Very Efficient High-Energy Phosphorescent Emission in Organic Materials." *Appl. Phys. Lett.*, 79, 2082-2084, 2001.

U.S. Appl. No. 11/924,891, filed Oct. 26, 2007, Kim et al., Samsung SDI Co., Ltd.
Registration Determination Certificate issued by the Korean Intellectual Property Office on Sep. 9, 2008.

*Primary Examiner*—Dawn Garrett
(74) *Attorney, Agent, or Firm*—Stein McEwen, LLP

(57) ABSTRACT

Provided are a carbazole-based compound represented by Formula 1 below and an organic light-emitting device including an organic layer including the carbazole-based compound:

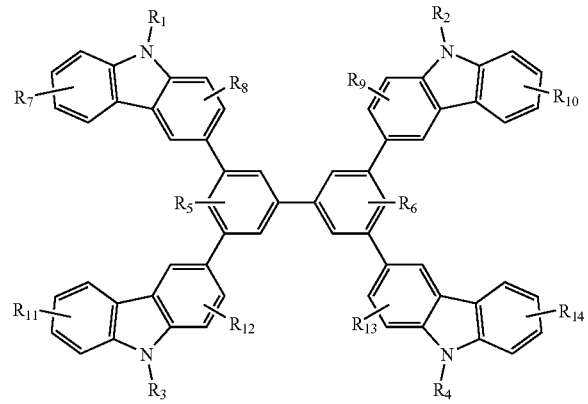

<Formula 1> wherein $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are as defined in the specification. The carbazole-based compound has good electrical characteristics and charge transport capability, and thus, is useful as a hole injection material, a hole transport material, and/or an emitting material for fluorescent or phosphorescent devices capable of producing light of a full spectrum of colors, including red, green, blue, and white, thereby making it possible to produce an organic light-emitting device with high efficiency, a low driving voltage, and high brightness.

16 Claims, 3 Drawing Sheets

FIG. 1

| |
|---|
| Second electrode |
| One or more organic layers, at least one of which contains the carbazole-based compound of Formula 1 |
| First electrode |

FIG. 2

| |
|---|
| Second electrode |
| Emitting layer |
| Hole injection layer |
| First electrode |

FIG. 3

| |
|---|
| Second electrode |
| Electron transport layer |
| Emitting layer |
| Hole transport layer |
| Hole injection layer |
| First electrode |

FIG. 4

| |
|---|
| Second electrode |
| Electron injection layer |
| Electron transport layer |
| Emitting layer |
| Hole transport layer |
| Hole injection layer |
| First electrode |

FIG. 5

| Second electrode |
|---|
| Electron transport layer |
| Emitting layer |
| Single layer having hole injection capability and hole transport capability |
| First electrode |

FIG. 6

| Second electrode |
|---|
| Electron injection layer |
| Electron transport layer |
| Emitting layer |
| Single layer having hole injection capability and hole transport capability |
| First electrode |

FIG. 7

| Second electrode |
|---|
| Hole blocking layer |
| Emitting layer |
| Electron blocking layer |
| Hole injection layer |
| First electrode |

CARBAZOLE-BASED COMPOUND AND ORGANIC LIGHT-EMITTING DEVICE INCLUDING ORGANIC LAYER INCLUDING THE CARBAZOLE-BASED COMPOUND

CROSS-REFERENCE TO RELATED APPLICATIONS

This application claims the benefit of Korean Application No. 2007-5817, filed Jan. 18, 2007, in the Korean Intellectual Property Office, the disclosure of which is incorporated herein by reference.

BACKGROUND OF THE INVENTION

1. Field of the Invention

Aspects of the present invention relate to a carbazole-based compound and an organic light-emitting device including an organic layer including the carbazole-based compound. More particularly, aspects of the present invention relate to a carbazole-based compound that has electrical stability, good charge transport capability, and a high glass transition temperature, and can prevent crystallization. Aspects of the present invention further relate to an organic light-emitting device including an organic layer including the carbazole-based compound.

2. Description of the Related Art

Organic light-emitting devices are self-emitting devices that have advantages such as a wide viewing angle, good contrast, and a rapid response time. Moreover, organic light-emitting devices show good driving voltage and response speed characteristics and can create polychromatic light. Thus, there has been an increasing interest in organic light-emitting devices and extensive research into these devices has been conducted.

Generally, organic light-emitting devices have a stacked structure including an anode, an emitting layer, and a cathode. A hole injection layer, a hole transport layer, or an electron injection layer may be further disposed between the anode and the emitting layer or between the emitting layer and the cathode to form an anode/hole transport layer/emitting layer/cathode structure, an anode/hole transport layer/emitting layer/electron injection layer/cathode structure, or the like.

A fluorene derivative and an anthracene derivative have been described as a material for forming a hole transport layer (U.S. Pat. Nos. 6,596,415 and 6,465,115).

However, organic light-emitting devices including hole transport layers formed of conventional hole transport layer materials have disadvantages in terms of lifetime, efficiency, and power consumption characteristics, and thus, there is room for improvement in conventional organic light-emitting devices.

SUMMARY OF THE INVENTION

Aspects of the present invention provide a material which has electrical stability, good charge transport capability, and a high glass transition temperature, can prevent crystallization, and is suitable as an organic layer material for fluorescent or phosphorescent devices capable of producing light of a full spectrum of colors, including red, green, blue, and white, and a method of preparing the same. Aspects of the present invention also provide an organic light-emitting device showing high efficiency, a low driving voltage, and high brightness, by virtue of employing an organic layer including the material.

According to an aspect of the present invention, there is provided a carbazole-based compound represented by Formula 1 below:

<Formula 1>

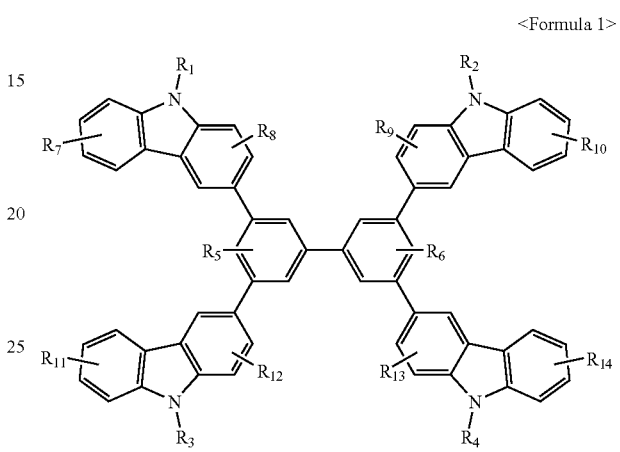

wherein, $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are each independently hydrogen, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, or a substituted or unsubstituted $C_2$-$C_{30}$ heteroaryl group, and adjacent groups selected from $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ may join together to form a saturated or unsaturated carbon ring.

According to another aspect of the present invention, there is provided an organic light-emitting device including a first electrode; a second electrode; and an organic layer interposed between the first electrode and the second electrode, the organic layer including the carbazole-based compound.

An organic light-emitting device including an organic layer including a carbazole-based compound of Formula 1 can show a low driving voltage, high brightness, high efficiency, high current density, etc.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 1 through 8 are views illustrating organic light-emitting devices according to embodiments of the present invention.

DETAILED DESCRIPTION OF THE EMBODIMENTS

Figure 8:
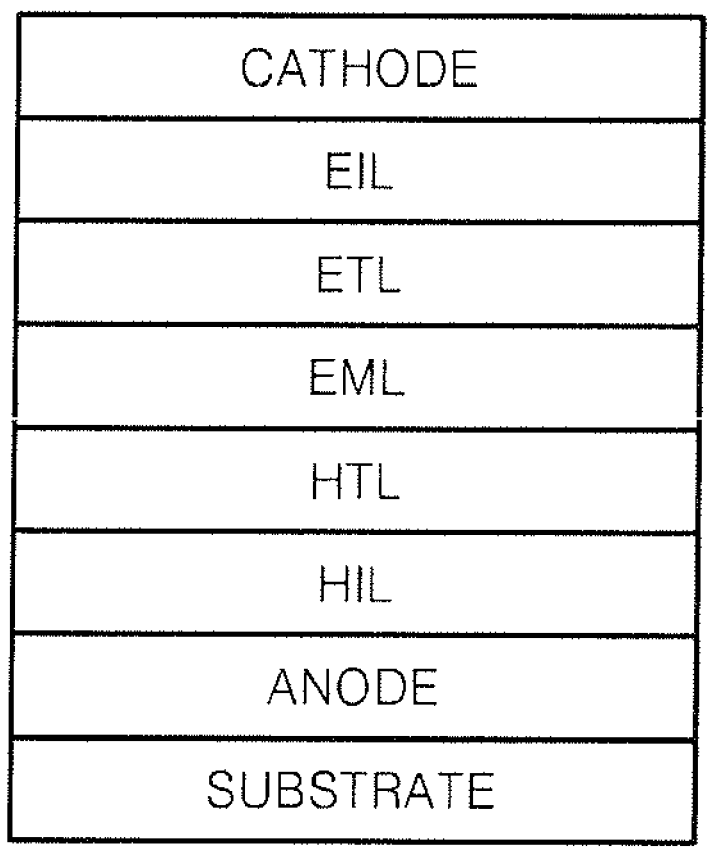

Reference will now be made in detail to the present embodiments of the present invention, examples of which are illustrated in the accompanying drawings, wherein like reference numerals refer to the like elements throughout. The embodiments are described below in order to explain the present invention by referring to the figures.

Aspects of the present invention provide a carbazole-based compound represented by Formula 1 below:

<Formula 1>

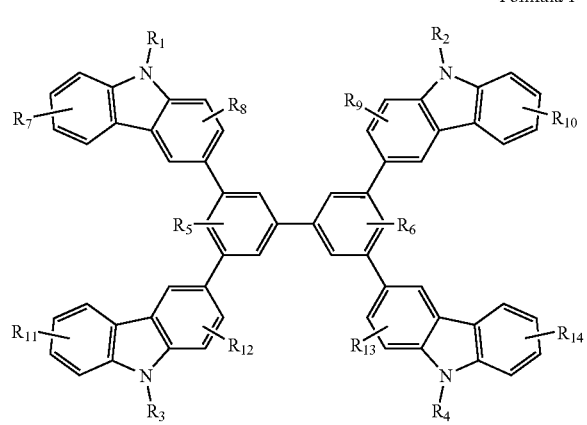

wherein $R_1, R_2, R_3, R_4, R_5, R_6, R_7, R_8, R_9, R_{10}, R_{11}, R_{12}, R_{13}$, and $R_{14}$ are each independently hydrogen, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, or a substituted or unsubstituted $C_2$-$C_{30}$ heteroaryl group, and wherein adjacent groups selected from $R_1, R_2, R_3, R_4, R_5, R_6, R_7, R_8, R_9, R_{10}, R_{11}, R_{12}, R_{13}$, and $R_{14}$ may join together to form a saturated or unsaturated carbon ring.

The carbazole-based compound of the Formula 1, which is structured such that four carbazole groups are connected to a biphenyl group, is a material that has electrical stability, good charge transport capability, and a high glass transition temperature, and that can prevent crystallization. The carbazole-based compound of Formula 1 is useful as a hole injection material, a hole transport material, and/or an emitting material, thereby making it possible to manufacture an organic light-emitting device with a high efficiency, a low driving voltage, and a high brightness.

As non-limiting examples, the carbazole-based compound of Formula 1 may be one selected from compounds represented by Formulae 2 through 4 below:

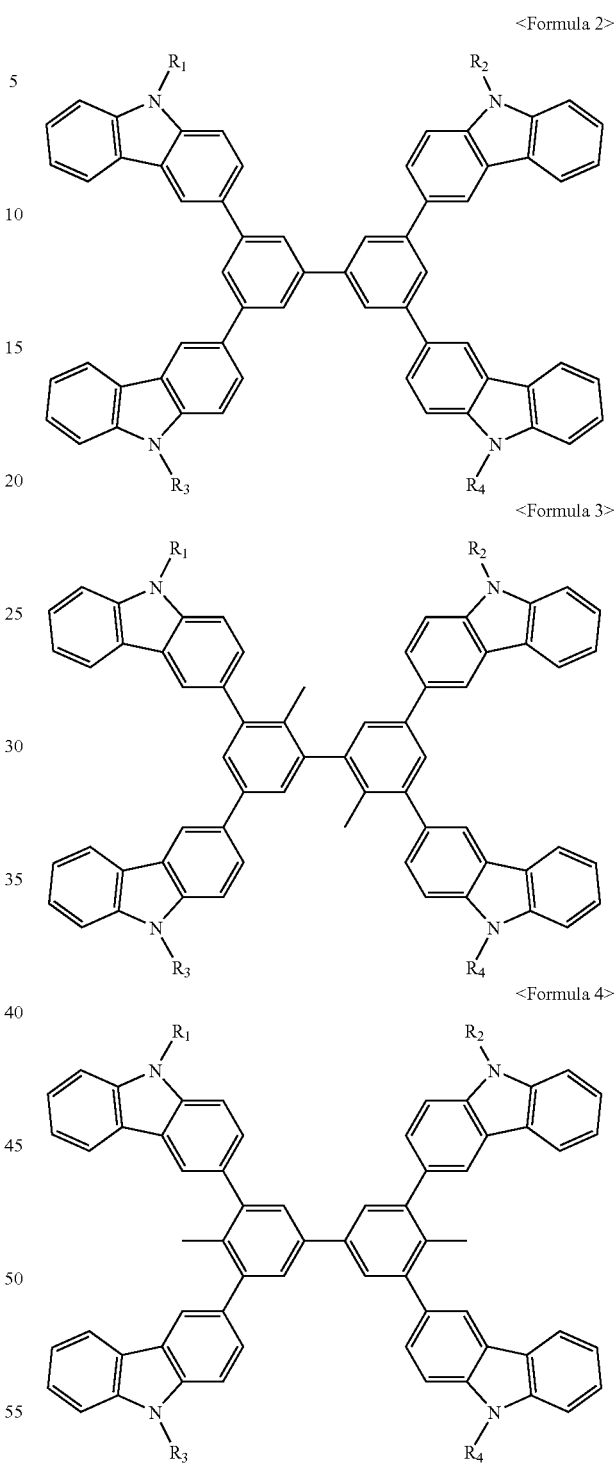

wherein $R_1, R_2, R_3$, and $R_4$ are each independently hydrogen, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, or a substituted or unsubstituted $C_2$-$C_{30}$ heteroaryl group.

As non-limiting examples, $R_1$, $R_2$, $R_3$, and $R_4$ may be each independently a substituted or unsubstituted $C_1$-$C_{10}$ alkyl group, a substituted or unsubstituted $C_1$-$C_{10}$ alkoxy group, a substituted or unsubstituted $C_6$-$C_{12}$ aryl group, a substituted or unsubstituted $C_6$-$C_{12}$ aryloxy group, or a substituted or unsubstituted $C_3$-$C_{12}$ heteroaryl group. As specific, non-limiting examples, $R_1$, $R_2$, $R_3$, and $R_4$ may be each independently a $C_1$-$C_{10}$ alkyl group, a phenyl group, a halophenyl group, a cyanophenyl group, a $C_1$-$C_{10}$ alkylphenyl group, a $C_1$-$C_{10}$ alkoxyphenyl group, a biphenyl group, a halobiphenyl group, a naphthyl group, a halonaphthyl group, a $C_1$-$C_{10}$ alkylnaphthyl group, or a $C_1$-$C_{10}$ alkoxynaphthyl group.

Non-limiting examples of an unsubstituted C1-C20 alkyl group used in the formulae herein include methyl, ethyl, propyl, isobutyl, sec-butyl, pentyl, iso-amyl, and hexyl. At least one hydrogen atom of the alkyl group may be substituted by a halogen atom, a hydroxy group, a nitro group, a cyano group, an amino group, an amidino group, hydrazine, hydrazone, a carboxyl group or its salt, a sulfonyl group or its salt, a phosphonyl group or its salt, a C1-C30 alkyl group, a C1-C30 alkenyl group, a C1-C30 alkynyl group, a C6-C30 aryl group, a C7-C30 arylalkyl group, a C2-C20 heteroaryl group, or a C3-C30 heteroarylalkyl group.

Non-limiting examples of an unsubstituted C1-C20 alkoxy group used in the formulae herein include methoxy, ethoxy, phenyloxy, cyclohexyloxy, naphthyloxy, isopropyloxy, and diphenyloxy. At least one hydrogen atom of the alkoxy group may be substituted by the same substituents as those recited in the above definition of the alkyl group.

The term "an unsubstituted C6-C20 aryl group," which may be used herein alone or in combination, refers to an aromatic carbocyclic system containing one or more rings. The rings may be attached to each other as a pendant group or may be fused. At least one hydrogen atom of the aryl group may be substituted by the same substituents as those recited in the above definition of the alkyl group.

The aryl group may be a phenyl group, an ethylphenyl group, an ethylbiphenyl group, o-, m-, and p-fluorophenyl groups, a dichlorophenyl group, a dicyanophenyl group, a trifluoromethoxyphenyl group, o-, m-, and p-tolyl groups, o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a methylnaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, etc.

Non-limiting examples of an unsubstituted aryloxy group used in the formulae herein include phenyloxy, naphthyleneoxy, and diphenyloxy. At least one hydrogen atom of the aryloxy group may be substituted by the same substituents as those recited in the above definition of the alkyl group.

The term "an unsubstituted heteroaryl group" as used herein refers to a monovalent monocyclic or bicyclic aromatic organic compound of 6-30 carbon atoms containing one, two or three heteroatoms selected from N, O, P, and S. At least one hydrogen atom of the heteroaryl group may be substituted by the same substituents as those recited in the above definition of the alkyl group.

Non-limiting examples of the heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, etc.

Examples of the carbazole-based compound of Formula 1 include, but are not limited to, compounds 1-27 below:

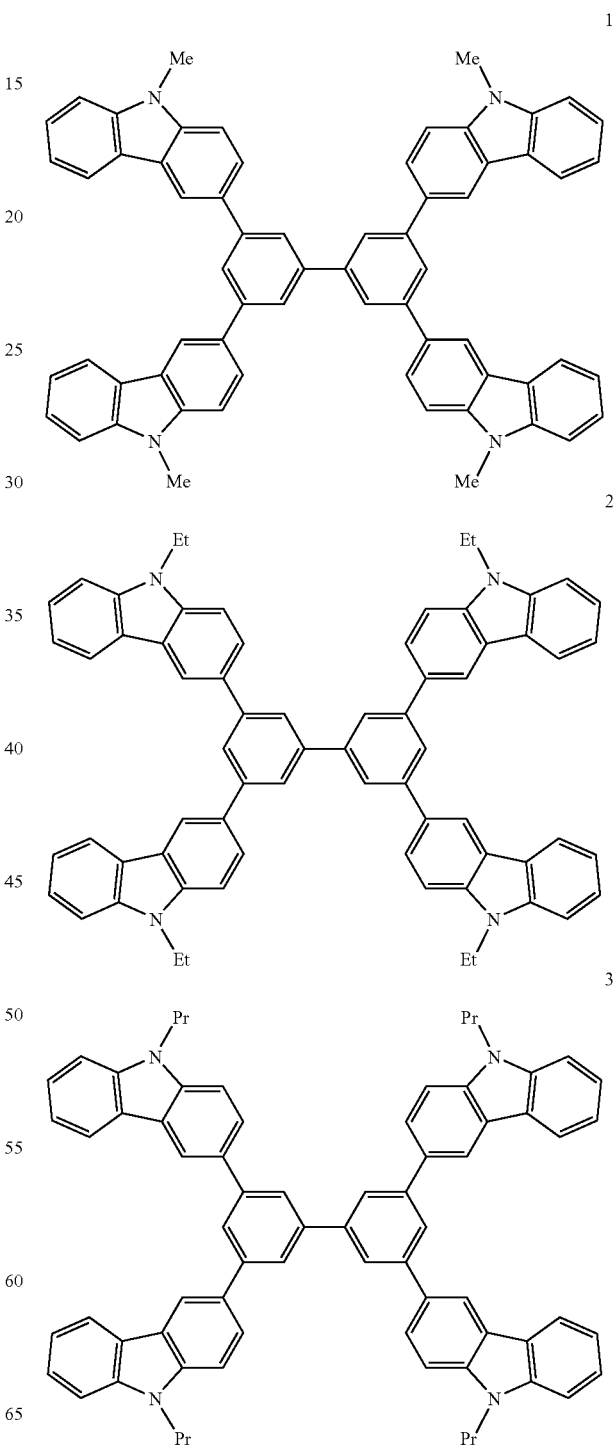

-continued
4
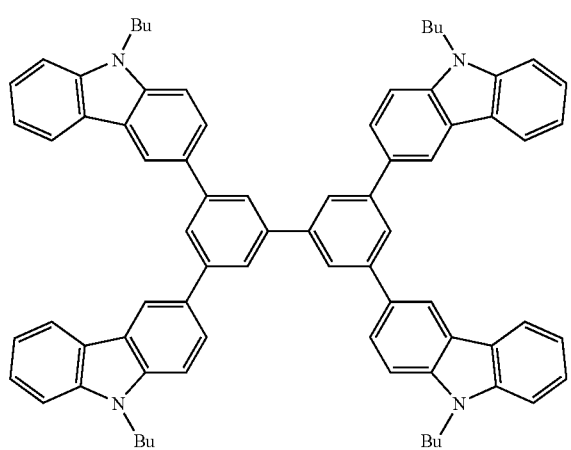
5
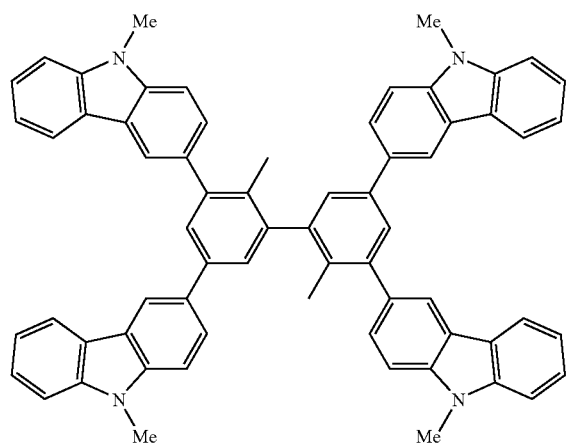
6
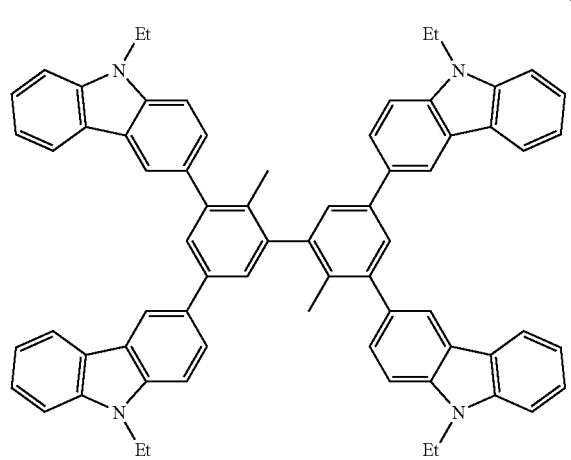
-continued
7
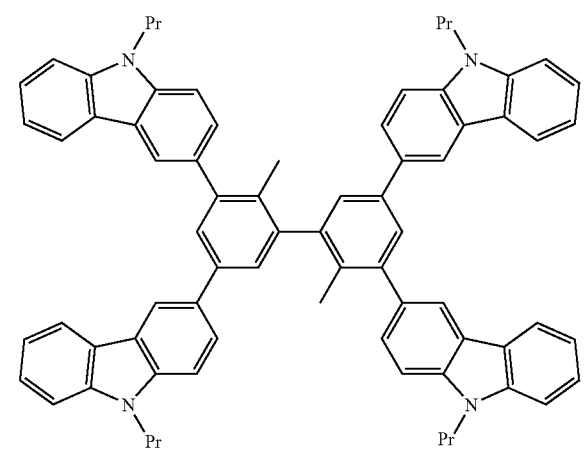
8
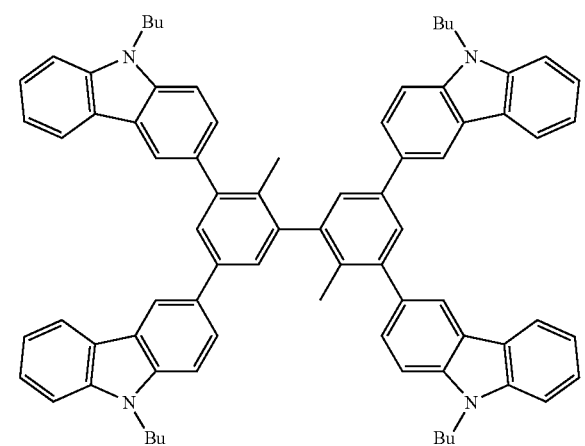
9
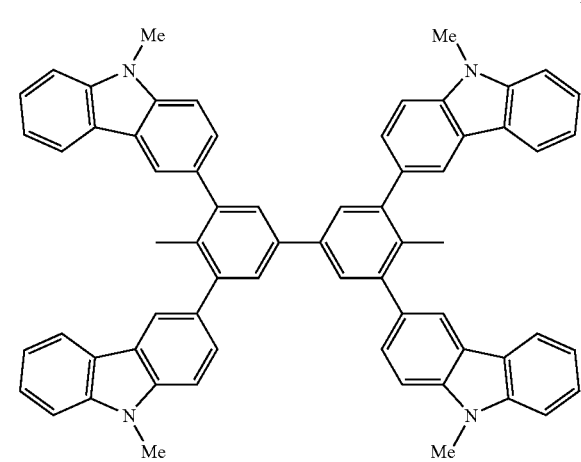

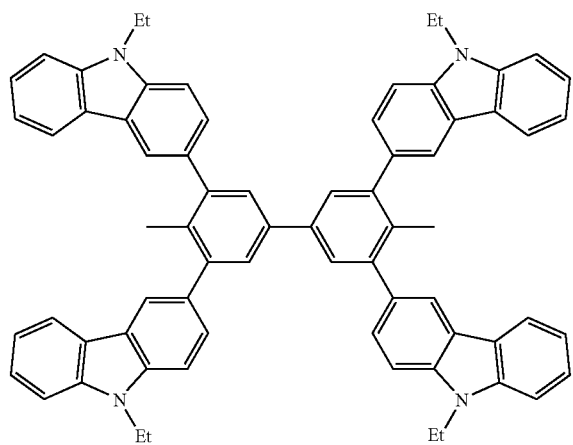
10
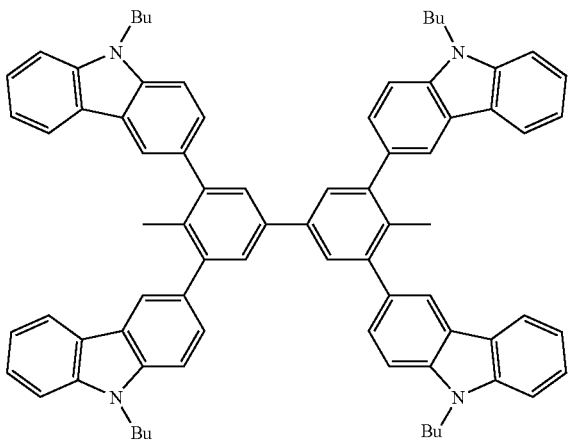
12
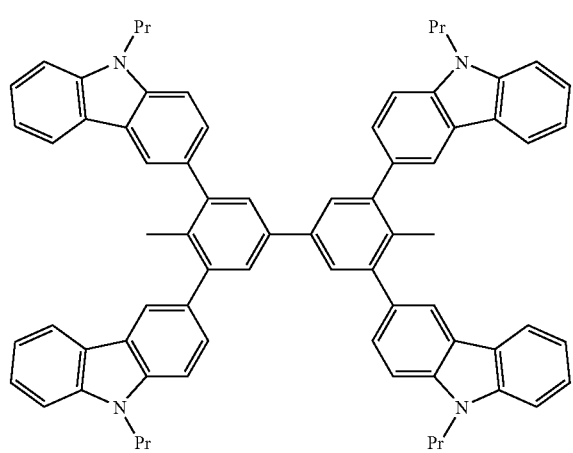
11
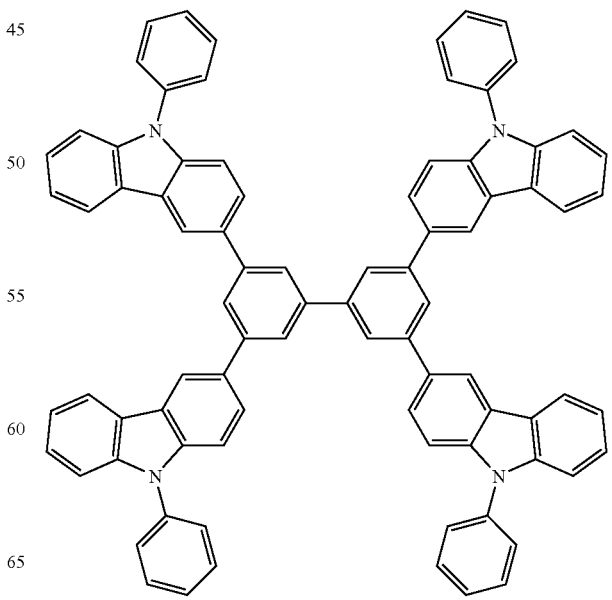
13

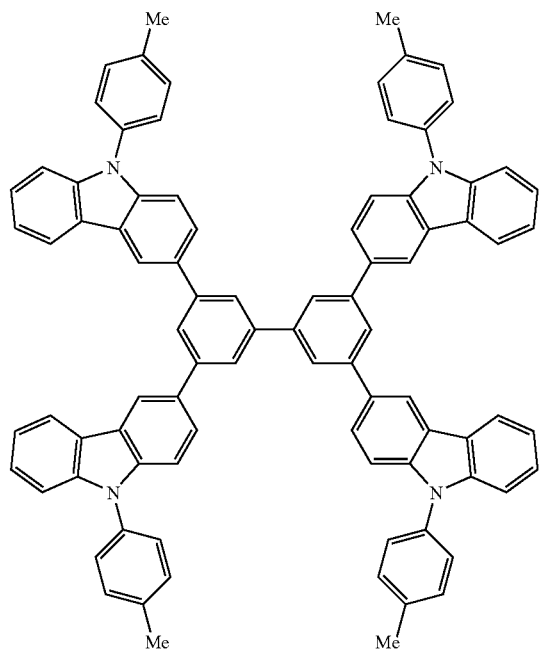
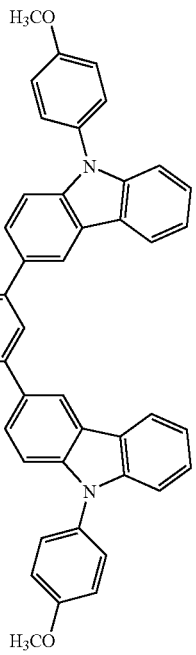
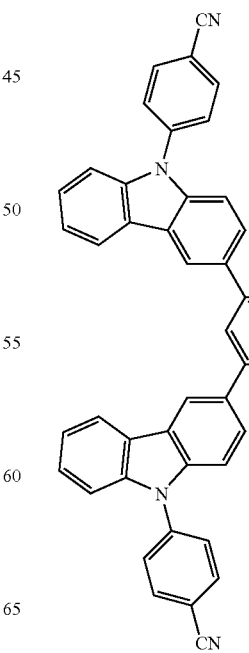
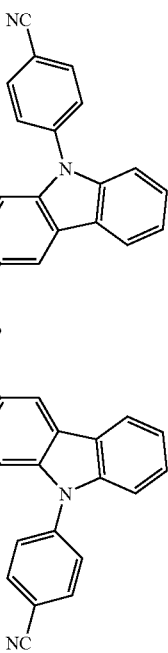

18
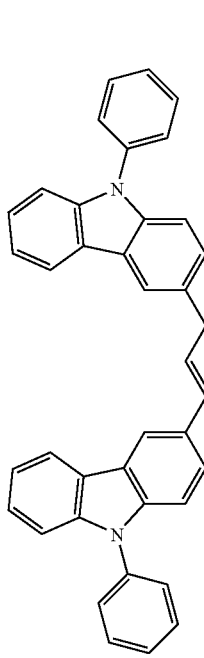
19
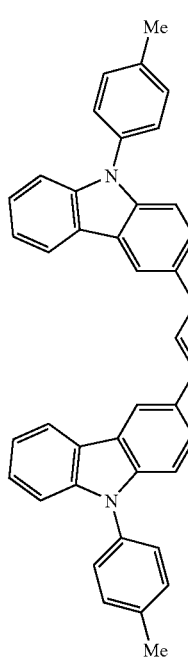 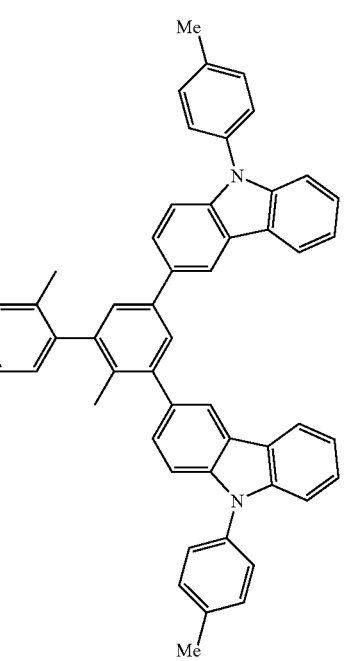
20
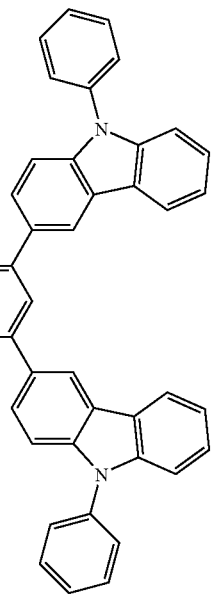 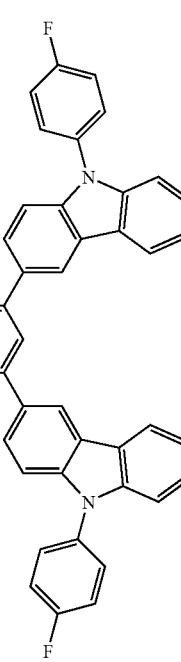
21
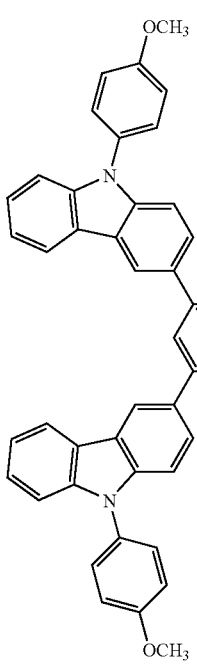 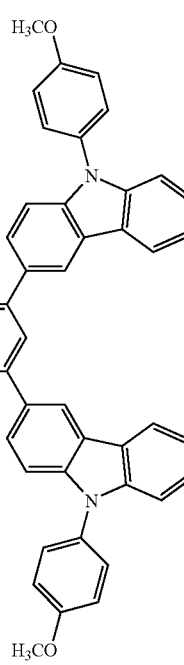

-continued
22
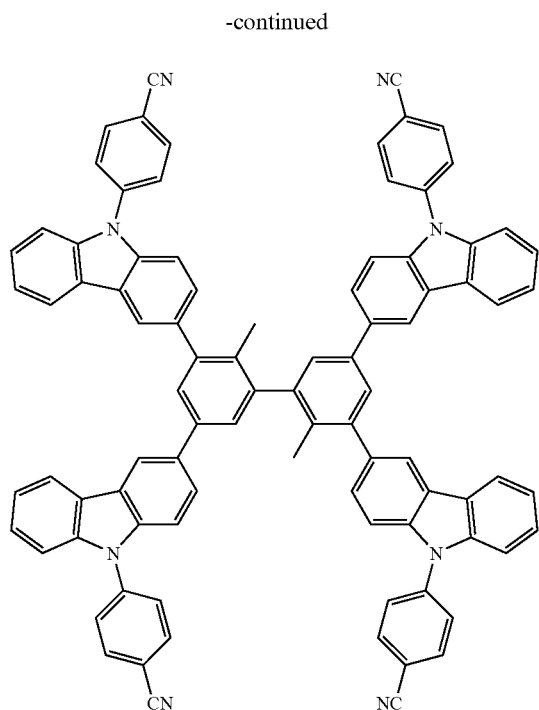
23
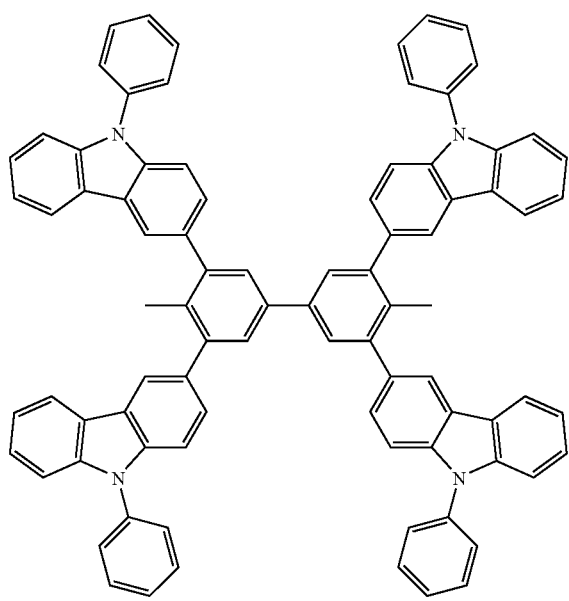
-continued
24
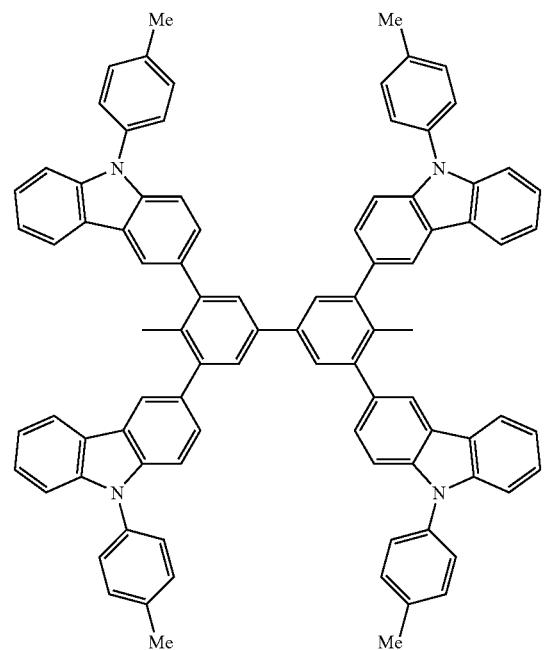
25
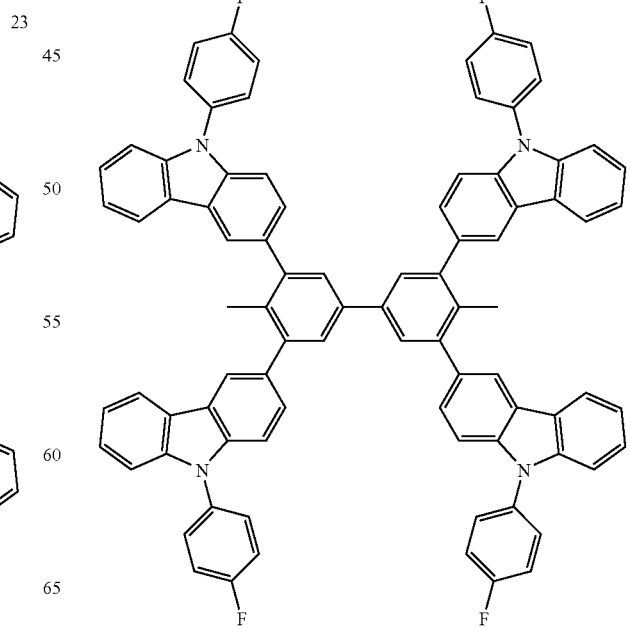

-continued

26

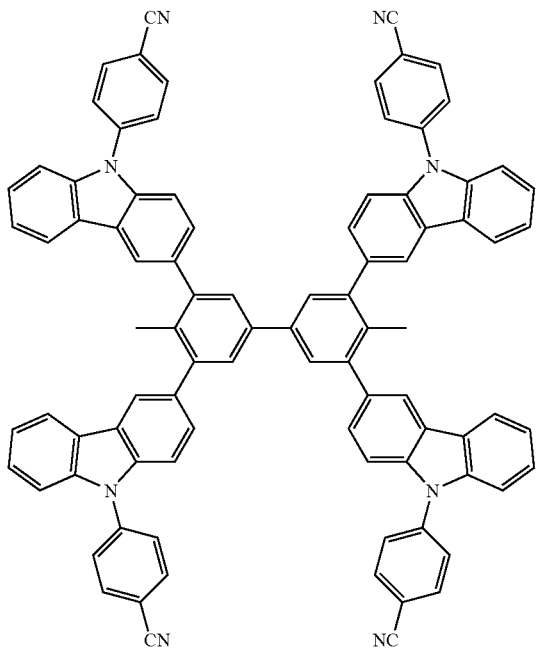

27

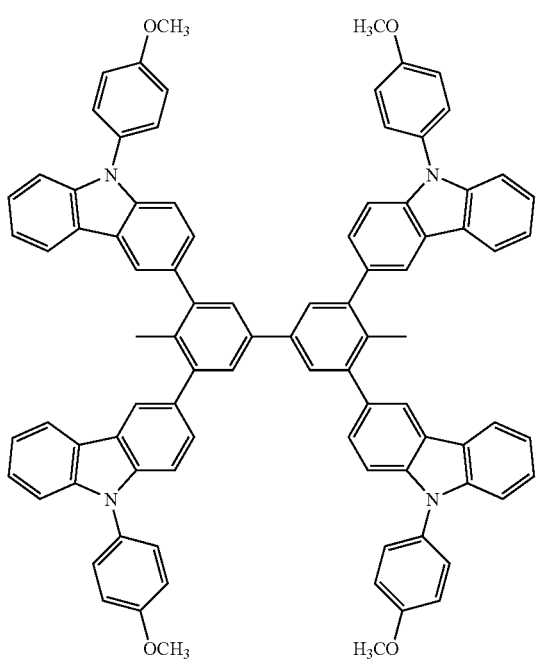

Aspects of the present invention also provide an organic light-emitting device. Examples of organic light-emitting devices are shown in FIGS. 1-8. For example, FIG. 1 shows an organic light-emitting device including: a first electrode, a second electrode, and one or more organic layers interposed between the first electrode and the second electrode, wherein at least one of the one or more organic layers includes a carbazole-based compound of Formula 1. The organic layer including the carbazole-based compound of Formula 1 may be a hole injection layer, a hole transport layer, or a single layer having hole injection capability and hole transport capability. The organic layer including the carbazole-based compound of Formula 1 may also, or alternatively, be an emitting layer. The emitting layer may include a phosphorescent or fluorescent material. The first electrode may be an anode and the second electrode may be a cathode. Alternatively, the first electrode may be a cathode and the second electrode may be an anode. Herein, when the term "interposed between" is used, such as in the phrase "an including a carbazole-based compound of Formula 1," it is to be understood that a single organic layer may be present between the first electrode and the second electrode or that other layers, including or not including the carbazole-based compound, may be present between the first electrode and the second electrode.

The above-described organic light-emitting device may further include at least one of a hole injection layer, a hole transport layer, an electron blocking layer, an emitting layer, a hole blocking layer, an electron transport layer, and an electron injection layer, when desired. For example, the organic light-emitting device according to aspects of the present invention may have a first electrode/hole injection layer/emitting layer/second electrode structure (FIG. 2), a first electrode/hole injection layer/hole transport layer/emitting layer/electron transport layer/second electrode structure (FIG. 3), or a first electrode/hole injection layer/hole transport layer/emitting layer/electron transport layer/electron injection layer/second electrode structure (FIG. 4). The organic light-emitting device may also have a first electrode/single layer having hole injection and hole transport capabilities/emitting layer/electron transport layer/second electrode structure (FIG. 5), or a first electrode/single layer having hole injection and hole transport capabilities/emitting layer/electron transport layer/electron injection layer/second electrode structure (FIG. 6). It is to be understood that either an electron blocking layer or a hole blocking layer or both can be used with any of the structures described above. As an example of an organic light-emitting device containing blocking layers, FIG. 7 shows an organic light-emitting device including a first electrode, a hole injection layer, an electron blocking layer, an emitting layer, a hole blocking layer and a second electrode.

Hereinafter, a method of manufacturing an organic light-emitting device according to an embodiment of the present invention will be described with reference to FIG. 8. Referring to FIG. 8, an organic light-emitting device is formed on a substrate and includes a first electrode (anode), a hole injection layer, a hole transport layer, an emitting layer, an electron transport layer, an electron injection layer, and a second electrode (cathode). As used herein, when it is mentioned that a first layer is "formed on" a second layer, or similar language, the first layer may be directly formed on the first layer or one or more additional layers may be between the first layer and the second layer.

First, a first electrode is formed on a substrate by deposition or sputtering using a first electrode material with a high work function. The first electrode may be an anode or a cathode.

The substrate may be a substrate commonly used in organic light-emitting devices. As a non-limiting example, the substrate may be a glass or transparent plastic substrate that is excellent in mechanical strength, thermal stability, transparency, surface smoothness, handling property, and water repellency. The first electrode material may be a material with good conductivity, e.g., indium tin oxide (ITO), indium zinc oxide (IZO), tin oxide ($SnO_2$), or zinc oxide (ZnO), and may form a transparent electrode or a reflective electrode.

Next, a hole injection layer (HIL) may be formed on the first electrode using any one of various methods, such as vacuum deposition, spin-coating, casting, or a Langmuir-Blodgett (LB) method.

If the hole injection layer is formed using a vacuum deposition process, the deposition conditions vary according to the type of a hole injection layer material, the structure and thermal characteristics of the hole injection layer, etc. As a non-limiting example, the hole injection layer may be deposited to a thickness of 10 Å to 5 μm at a deposition rate of 0.01 to 100 Å/sec, at a temperature of 100 to 500° C., and in a vacuum level of $10^{-8}$ to $10^{-3}$ torr.

If the hole injection layer is formed using a spin-coating process, the coating conditions vary according to the type of a hole injection layer material, the structure and thermal characteristics of the hole injection layer, etc. As a non-limiting example, the spin-coating may be performed at a coating speed of about 2,000 to 5,000 rpm, and, after the spin-coating, a thermal treatment may be performed at a temperature of about 80 to 200° C. for the purpose of solvent removal.

The hole injection layer material may be a carbazole-based compound of Formula 1 as described above. In addition or alternatively, the hole injection layer material may be a known hole injection layer material, e.g., a phthalocyanine compound (e.g., copper phthalocyanine) disclosed in U.S. Pat. No. 4,356,429, a Starburst-type amine derivative (e.g., TCTA, m-MTDATA, or m-MTDAPB) disclosed in *Advanced Material*, 6, p. 677 (1994), or a soluble conductive polymer, e.g., polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), or polyaniline/poly(4-styrenesulfonate) (PANI/PSS).

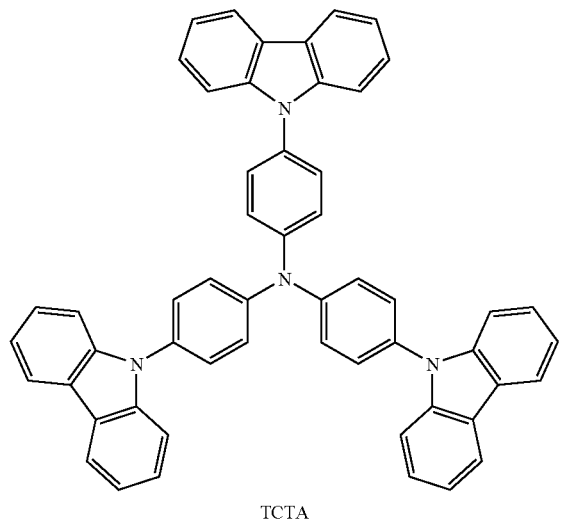

TCTA

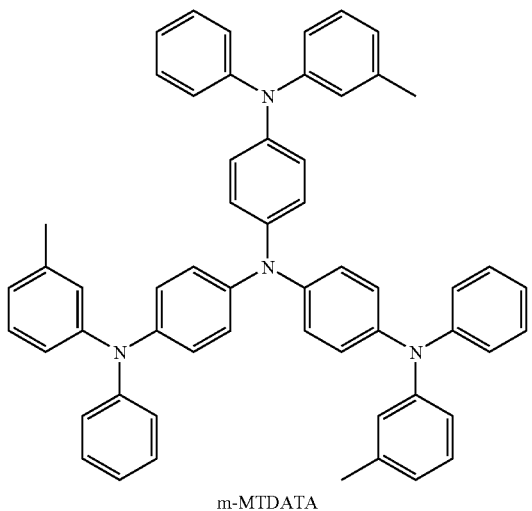

m-MTDATA

The hole injection layer may be formed to a thickness of about 100 to 10,000 Å. As a non-limiting example, the hole injection layer may be formed to a thickness of 100 to 1,000 Å. If the thickness of the hole injection layer is less than 100 Å, hole injection characteristics may be lowered. On the other hand, if the thickness of the hole injection layer exceeds 10,000 Å, the driving voltage may be increased.

Next, a hole transport layer (HTL) may be formed on the hole injection layer using any one of various methods, such as vacuum deposition, spin-coating, casting, or an LB method. When forming the hole transport layer using vacuum deposition or spin-coating, the deposition or coating conditions vary according to the type of compound used, but are generally about the same as those used for the formation of the hole injection layer.

The hole transport layer material may be a carbazole-based compound of Formula 1 as described above. In addition or alternatively, the hole transport layer material can be a known hole transport layer material, e.g., a carbazole derivative such as N-phenylcarbazole or polyvinylcarbazole; an amine derivative having an aromatic fused ring such as 4,4'-bis[N-(1-naphthyl)-N-phenylamino]biphenyl (NPB), N,N'-bis(3-methylphenyl)-N,N'-diphenyl-[1,1-biphenyl]-4,4'-diamine (TPD), or N,N'-di(naphthalene-1-yl)-N,N'-diphenylbenzidine (α-NPD); etc.

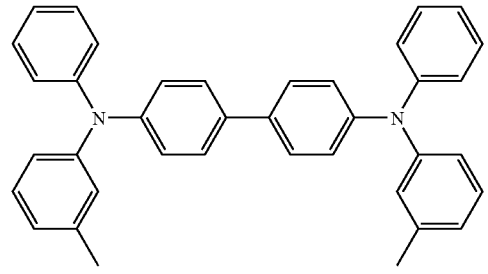

TPD

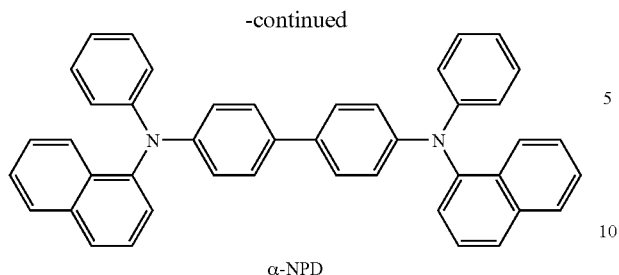

α-NPD

The hole transport layer may be formed to a thickness of about 50 to 1,000 Å. As a non-limiting example, the hole transport layer may be formed to a thickness of 100 to 600 Å. If the thickness of the hole transport layer is less than 50 Å, hole transport characteristics may be lowered. On the other hand, if the thickness of the hole transport layer exceeds 1,000 Å, the driving voltage may be increased.

Next, an emitting layer (EML) may be formed on the hole transport layer using vacuum deposition, spin-coating, casting, or an LB method. If the emitting layer is formed using vacuum deposition or spin-coating, the deposition or coating conditions vary according to the type of compound used, but are generally about the same as those used for formation of the hole injection layer.

The emitting layer may include a carbazole-based compound of Formula 1 as described above. For example, the carbazole-based compound of Formula 1 may be a host material in the emitting layer. In addition or alternatively, the emitting layer may be formed of various known emitting materials or known host/dopants. With respect to a dopant, known fluorescent or phosphorescent dopants can be used.

Alq$_3$, 4,4'-N,N'-dicarbazole-biphenyl (CBP), poly(n-vinylcarbazole) (PVK), distyrylarylene (DSA), IDE215 (Idemitsu), etc. may be used as a host, but the present invention is not limited thereto.

The dopant may be a fluorescent dopant such as IDE102, IDE105, and IDE118, which are commercially available from Idemitsu, or a phosphorescent dopant such as Ir(ppy)$_3$ (ppy: phenylpyridine)(green), (4,6-F2 ppy)$_2$Irpic (reference: Chihaya Adachi etc. Appl. Phys. Lett., 79, 2082-2084, 2001), TEB002 (Covion Co.), platinum(ii) octaethylporphyrin (PtOEP), a compound represented by Formula 6 below (see Korean Patent Laid-Open Publication No. 2005-0078472), Firpric, or a red phosphorescent dopant (RD1, UDC), but the present invention is not limited thereto.

<Formula 6>

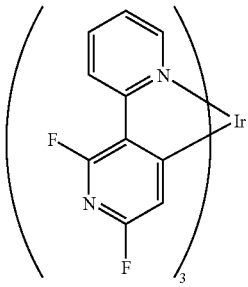

Firpic

The amount of dopant may be 0.1 to 20 parts by weight, based on 100 parts by weight (i.e., the total weight of a host and the dopant) of an emitting layer forming material. As a non-limiting example, the amount of dopant may be 0.5 to 12 parts by weight, based on 100 parts by weight of an emitting layer forming material If the amount of dopant is less than 0.1 parts by weight, the dopant addition effect may be insufficient. On the other hand, if the amount of dopant exceeds 20 parts by weight, concentration quenching of both phosphorescence and fluorescence may occur.

The emitting layer may be formed to a thickness of about 100 to 1,000 Å. As a non-limiting example, the emitting layer may be formed to a thickness of 200 to 600 Å. If the thickness of the emitting layer is less than 100 Å, emission characteristics may be lowered. On the other hand, if the thickness of the emitting layer exceeds 1,000 Å, the driving voltage may be increased.

If the emitting layer includes a phosphorescent dopant, a hole blocking layer (HBL) may be formed on the emitting layer in order to prevent the diffusion of triplet excitons or holes into an electron transport layer. The hole blocking layer material is not particularly limited and may be optionally selected from known hole blocking layer materials. For example, an oxadiazole derivative, a triazole derivative, a phenanthroline derivative, a hole blocking material disclosed in JP 11-329734(A1), Balq, BCP, etc. may be used.

The hole blocking layer may be formed to a thickness of about 50 to 1,000 Å. As a non-limiting example, the hole blocking layer may be formed to a thickness of 100 to 300 Å. If the thickness of the hole blocking layer is less than 50 Å, hole blocking characteristics may be lowered. On the other hand, if the thickness of the hole blocking layer exceeds 1,000 Å, the driving voltage may be increased.

Next, an electron transport layer (ETL) may be formed using any one of various methods, such as vacuum deposition, spin-coating, or casting. If the electron transport layer is formed using vacuum deposition or spin-coating, the deposition or coating conditions vary according to the type of compound used, but are generally about the same as those used for formation of the hole injection layer.

The electron transport layer material is not particularly limited and may be optionally selected from known electron transport layer materials. For example, a known material such as a quinoline derivative, in particular, tris(8-quinolinolate) aluminum (Alq$_3$), or TAZ may be used.

The electron transport layer may be formed to a thickness of about 100 to 1,000 Å. As a non-limiting example, the electron transport layer may be formed to a thickness of 200 to 500 Å. If the thickness of the electron transport layer is less than 100 Å, electron transport characteristics may be lowered. On the other hand, if the thickness of the electron transport layer exceeds 1,000 Å, the driving voltage may be increased.

An electron injection layer (EIL) may be formed on the electron transport layer in order to facilitate the injection of electrons from a cathode.

The electron injection layer material may be optionally selected from known materials such as LiF, NaCl, CsF, $Li_2O$, or BaO. The deposition or coating conditions of the electron injection layer vary according to the type of compound used, but are generally about the same as those used for formation of the hole injection layer.

The electron injection layer may be formed to a thickness of about 1 to 100 Å. As a non-limiting example, the electron injection layer may be formed to a thickness of 5 to 90 Å. If the thickness of the electron injection layer is less than 1 Å, electron injection characteristics may be lowered. On the other hand, if the thickness of the electron injection layer exceeds 100 Å, the driving voltage may be increased.

Finally, a second electrode may be formed on the electron injection layer using vacuum deposition or sputtering. The second electrode may be used as a cathode or an anode. The material for forming the second electrode may be a metal or alloy with a low work function, an electroconductive compound, or a mixture thereof. For example, the second electrode material may be lithium (Li), magnesium (Mg), aluminum (Al), aluminum-lithium (Al—Li), calcium (Ca), magnesium-indium (Mg—In), magnesium-silver (Mg—Ag), etc. The second electrode may also be a transmissive cathode formed of ITO or IZO to provide a front-emission type device.

Hereinafter, exemplary synthesis examples of compounds 1, 13, 18, 20, and 23 and working examples will be described. The following examples are for illustrative purposes only and are not intended to limit the scope of the invention.

EXAMPLES

Synthesis Example 1

Synthesis of Compound 1

Compound 1 was synthesized according to Reaction Scheme 1 below.

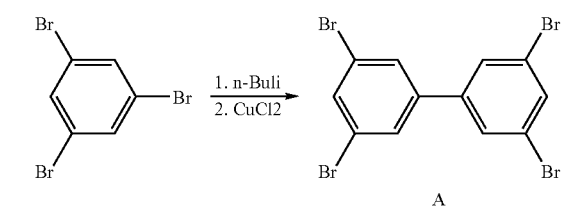

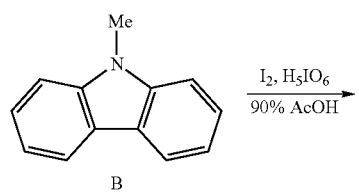

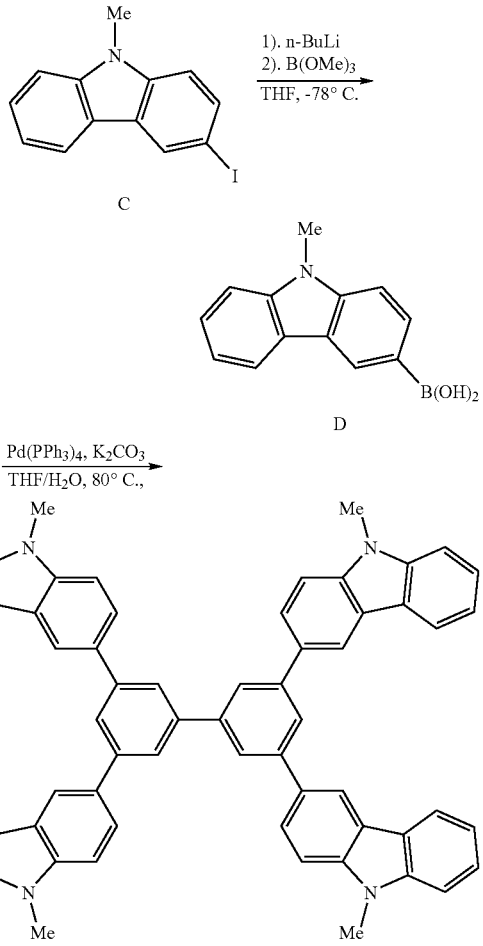

Synthesis of Intermediate A 1,3,5-tribromobenzene (6.3 g, 20 mmol) was dissolved in diethylether (50 ml). The reaction solution was cooled to −78° C., and n-butyllithium (8.8 ml, 22 mmol, 2.5M in hexane) was gradually added thereto. The reaction mixture was stirred at −78° C. for one hour, and copper chloride (II) (2.96 g, 22 mmol) was added thereto at −78° C. The reaction solution was stirred for five hours and washed with distilled water and ethylacetate at room temperature. The obtained ethylacetate layer was dried over $MgSO_4$, and then dried under a reduced pressure to obtain a crude product. The crude product was purified by silica gel column chromatography to give intermediate A as a white solid (3.74 g, yield: 80%). The structure of intermediate A was determined by $^1H$ NMR. $^1H$ NMR ($CDCl_3$, 300 MHz) δ (ppm) 7.69 (s, 2H), 7.58 (s, 4H); $^{13}C$ NMR ($CDCl_3$, 100 MHz) δ (ppm) 141.7, 133.8, 128.9, 123.5.

Synthesis of Intermediate B

Carbazole (16.7 g, 100 mmol), iodomethane (18.5 g, 130 mmol) and $K_2CO_3$ (138 g, 1.0 mol) were dissolved in dimethylformamide (DMF) (500 ml), and the reaction mixture was stirred at room temperature for eight hours. After the reaction was terminated, a solid material was filtered out. The resultant solution was extracted three times with diethylether (300 ml). The collected diethylether layer was washed with excess distilled water, dried over MgSO$_4$, filtered, and dried under a reduced pressure to obtain a crude product. The crude product was purified by silica gel column chromatography to give intermediate B (15.8 g, yield: 87%). The structure of intermediate B was determined by $^1$H NMR. $^1$H NMR (CDCl$_3$, 300 MHz) δ (ppm) 8.22 (d, 2H), 7.41 (d, 2H), 7.35-7.28 (m, 4H), 3.71 (s, 3H); $^{13}$C NMR (CDCl$_3$, 100 MHz) δ (ppm) 140.5, 125.6, 122.5, 120.0, 118.7, 109.5, 29.5.

Synthesis of Intermediate C

Carbazole (2.433 g, 10 mmol) was added to an 80% acetic acid (100 ml), and iodine (I$_2$) (1.357 g, 5.35 mmol) and ortho-periodinic acid (H$_5$IO$_6$) (0.333 g, 1.46 mmol) in a solid phase were added thereto. The reaction mixture was stirred at 80° C. under a nitrogen atmosphere for three hours. After the reaction was terminated, the reaction solution was extracted three times with ethylether (50 ml). The collected organic layer was dried over magnesium sulfate to evaporate a solvent. The resultant residue was purified by silica gel column chromatography to give intermediate C (2.61 g, yield: 85%). The structure of intermediate C was determined by $^1$H NMR. $^1$H NMR (CDCl$_3$, 300 MHz) δ (ppm) 8.32 (s, 1H), 7.95 (d, 1H), 7.62-7.55 (m, 2H), 7.38 (d, 1H), 7.31-7.45 (m, 2H), 3.66 (s, 3H); $^{13}$C NMR (CDCl$_3$, 100 MHz) δ (ppm) 141.5, 138.9, 129.2, 126.4, 124.9, 123.1, 122.3, 119.2, 118.8, 113.2, 108.5, 85.8, 30.5.

Synthesis of Intermediate D

Intermediate C (2.25 g, 7.34 mmol) was added to THF (50 ml), and n-butyllithium (2.5M in hexane) (3.9 ml, 9.55 mmol) was dropwise added thereto at −78° C. The reaction mixture was stirred for one hour, and trimethylborate (2.5 ml, 22.0 mmol) was added thereto. The reaction solution was heated to room temperature, stirred for one hour, and hydrolyzed with a 2N HCl solution. The aqueous layer was extracted three times with ethylacetate (20 ml). The collected organic layer was dried over magnesium sulfate to evaporate a solvent. The resultant residue was purified by silica gel column chromatography to give intermediate D as a white solid (0.89 g, yield: 54%). The structure of intermediate D was determined by $^1$H NMR. $^1$H NMR (CDCl$_3$, 300 MHz) δ (ppm) 8.11 (d, 1H), 8.09 (s, 2H), 7.93 (dd, 1H), 7.67 (dd, 1H), 7.58 (d, 1H), 7.44-7.37 (m, 1H), 7.32-7.25 (m, 2H), 30.7; $^{13}$C NMR (CDCl$_3$, 100 MHz) δ (ppm) 144.2, 140.1, 131.2, 130.6, 129.8, 129.5, 128.4, 127.2, 126.4, 125.8, 120.4, 119.7, 109.3, 100.1, 95.5, 86.5, 31.1.

Synthesis of Compound 1

Intermediate D (1.0 g, 4.4 mmol) and intermediate A (0.47 g, 1 mmol) were dissolved in THF (10 ml), and tetrakistriphenylphosphine palladium (92 mg, 0.08 mmol) and a solution of potassium carbonate (1.4 g, 10 mmol) in distilled water (10 ml) were sequentially added thereto. The reaction mixture was stirred at 75° C. for 12 hours. The reaction solution was extracted three times with ethylacetate (10 ml). The collected organic layer was dried over magnesium sulfate to evaporate a solvent. The resultant residue was purified by silica gel column chromatography to give compound 1 as a white solid (0.583 g, yield: 67%). The structure of compound 1 was determined by $^1$H NMR. $^1$H NMR (CDCl$_3$, 300 MHz) δ (ppm) 8.04 (d, 4H), 7.88 (d, 4H), 7.86-7.83 (m, 6H), 7.40 (d, 2H), 7.38 (d, 2H), 7.36-7.32 (m, 10H), 7.28-7.24 (m, 4H), 3.71 (s, 12H); $^{13}$C NMR (CDCl$_3$, 100 MHz) δ (ppm) 145.9, 140.3, 134.5, 130.4, 130.2, 127.4, 126.9, 126.8, 125.2, 121.3, 121.1, 119.1, 118.5, 117.6, 110.2, 109.0, 31.1.

Synthesis Example 2

Synthesis of Compound 13

Compound 13 was synthesized according to Reaction Scheme 2 below.

<Reaction Scheme 2>

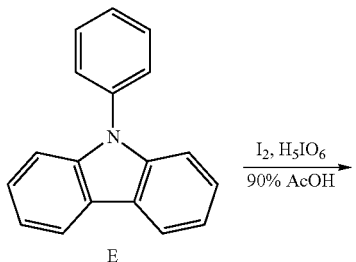

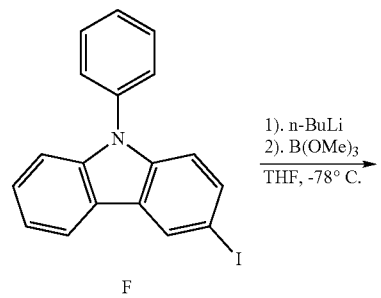

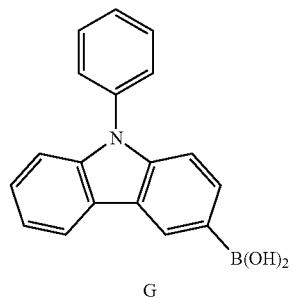

A + G $\xrightarrow{\text{Pd(PPh}_3\text{)}_4, \text{K}_2\text{CO}_3}{\text{THF/H}_2\text{O}, 80° \text{C.}}$

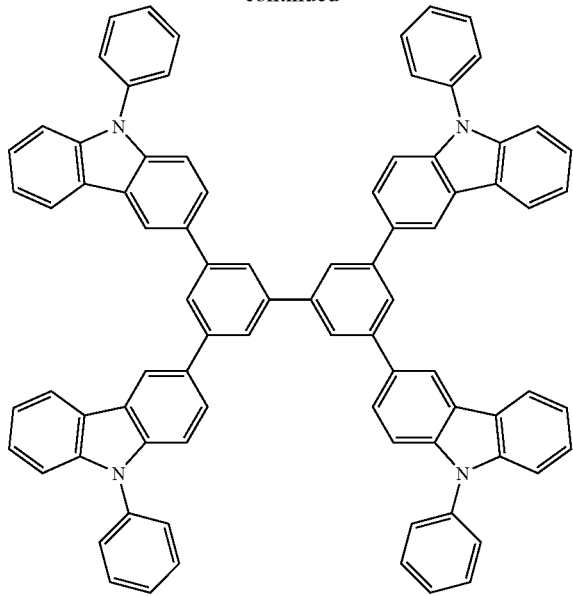

13

Synthesis of Intermediate E

Carbazole (16.7 g, 100 mmol), iodobenzene (26.5 g, 130 mmol), CuI (1.9 g, 10 mmol), $K_2CO_3$ (138 g, 1 mol), and 18-Crown-6 (530 mg, 2 mmol) were dissolved in DMPU (500 ml), and the reaction mixture was heated at 170° C. for eight hours. The reaction solution was cooled to room temperature and a solid material was filtered out. A trace amount of an ammonia solution was added to the filtrate, and the resultant solution was extracted three times with diethylether (300 ml). The obtained diethylether layer was dried over magnesium sulfate and then dried under a reduced pressure to obtain a crude product. The crude product was purified by silica gel column chromatography to give intermediate E as a white solid (22 g, yield: 90%). The structure of intermediate E was determined by $^1$H NMR. $^1$H NMR (CDCl$_3$, 300 MHz) δ (ppm) 8.12 (d, 2H), 7.58-7.53 (m, 4H), 7.46-7.42 (m, 1H), 7.38 (d, 4H), 7.30-7.26 (m, 2H); $^{13}$C NMR (CDCl$_3$, 100 MHz) δ (ppm) 141.0, 137.9, 130.0, 127.5, 127.3, 126.0, 123.5, 120.4, 120.0, 109.9.

Synthesis of Intermediate F

Intermediate E (2.433 g, 10 mmol) was added to an 80% acetic acid (100 ml), and iodine (I$_2$) (1.357 g, 5.35 mmol) and ortho-periodinic acid (H$_5$IO$_6$) (0.333 g, 1.46 mmol) in a solid phase were added thereto. The reaction mixture was stirred at 80° C. under a nitrogen atmosphere for two hours. After the reaction was terminated, the reaction solution was extracted three times with ethylether (50 ml). The collected organic layer was dried over magnesium sulfate to evaporate a solvent. The resultant residue was purified by silica gel column chromatography to give intermediate F as a white solid (3.23 g, yield: 87%). The structure of intermediate F was determined by $^1$H NMR. $^1$H NMR (CDCl$_3$, 300 MHz) δ (ppm) 8.43 (d, 1H), 8.05 (d, 1H), 7.62 (dd, 1H), 7.61-7.75 (m, 2H), 7.51-7.43 (m, 3H), 7.41-7.35 (m, 2H), 7.27 (dd, 1H), 7.14 (d, 1H)

Synthesis of Intermediate G

Intermediate F (2.71 g, 7.34 mmol) was added to THF (50 ml), and n-butyllithium (2.5M in hexane) (3.9 ml, 9.55 mmol) was dropwise added thereto at −78° C. The reaction mixture was stirred for one hour, and trimethylborate (2.5 ml, 22.0 mmol) was added thereto. The reaction solution was heated to room temperature, stirred for one hour, and hydrolyzed with a 2N HCl solution. An aqueous layer was extracted three times with ethylacetate (20 ml). The collected organic layer was dried over magnesium sulfate to evaporate a solvent. The resultant residue was purified by silica gel column chromatography to give intermediate G as a white solid (1.07 g, yield: 51%). The structure of intermediate G was determined by $^1$H NMR. $^1$H NMR (CDCl$_3$, 300 MHz) δ (ppm) 8.11 (d, 2H), 8.09 (s, 2H), 7.67 (d, 2H), 7.52-7.47 (m, 4H), 7.38-7.31 (m, 4H); $^{13}$C NMR (CDCl$_3$, 100 MHz) δ (ppm) 143.2, 140.3, 137.6, 131.2, 130.6, 129.8, 129.5, 128.4, 127.4, 127.1, 126.3, 124.8, 119.2, 119.0, 109.6, 99.6, 95.3, 90.5.

Synthesis of Compound 13

Intermediate G (1.26 g, 4.4 mmol) and the intermediate A (0.47 g, 1 mmol) were dissolved in THF (10 ml), and tetrakistriphenylphosphine palladium (92 mg, 0.08 mmol) and a solution of potassium carbonate (1.4 g, 10 mmol) in distilled water (10 ml) were sequentially added thereto. The reaction mixture was stirred at 75° C. for 12 hours. The reaction solution was extracted three times with ethylacetate (10 ml). The collected organic layer was dried over magnesium sulfate to evaporate a solvent. The resultant residue was purified by silica gel column chromatography to give compound 13 as a white solid (0.79 g, yield: 71%). The structure of compound 13 was determined by $^1$H NMR. $^1$H NMR (CDCl$_3$, 300 MHz) δ (ppm) 8.16 (d, 2H), 8.14 (s, 2H), 7.90-7.86 (m, 8H), 7.83 (t, 2H), 7.79 (d, 4H), 7.52-7.47 (m, 12H), 7.36-7.27 (m, 20H), 7.14 (dd, 4H); $^{13}$C NMR (CDCl$_3$, 100 MHz) δ (ppm) 144.8, 141.0, 137.0, 135.2, 131.9, 130.2, 129.8, 127.4, 127.1, 127.0, 126.8, 126.3, 125.2, 120.4, 119.9, 118.6, 118.3, 117.1, 114.2, 108.9.

Synthesis Example 3

Synthesis of Compound 18

Compound 18 was synthesized according to Reaction Scheme 3 below.

<Reaction Scheme 3>

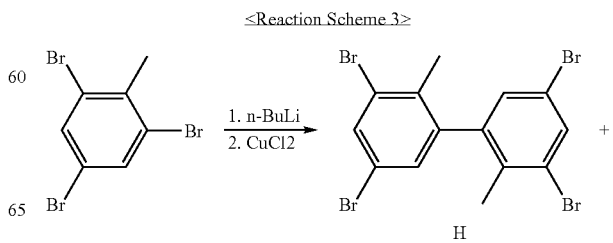

H

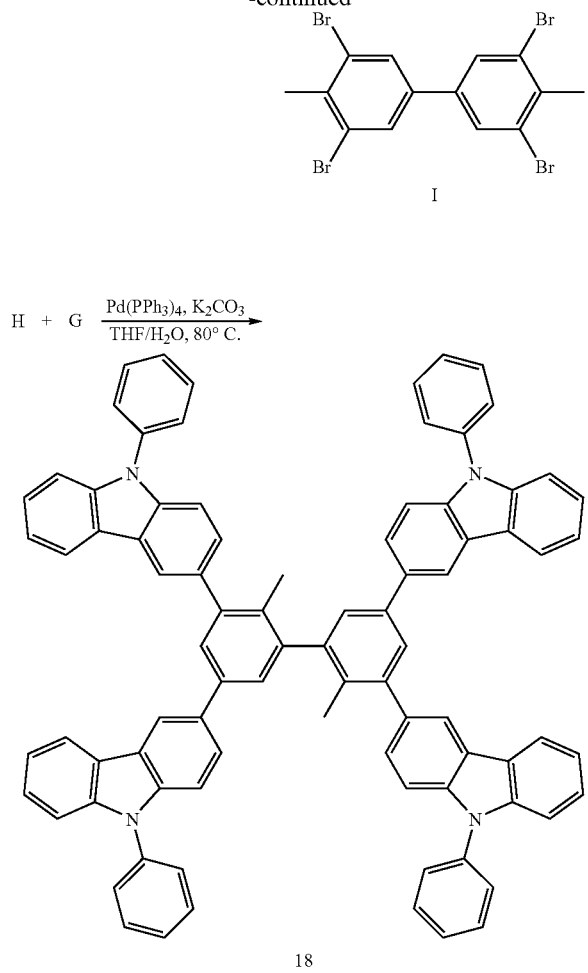

Synthesis of Intermediates H and I 2,4,6-tribromotoluene (3.3 g, 10 mmol) was dissolved in diethylether (30 ml). The reaction solution was cooled to −78° C., and n-butyllithium (4.4 ml, 11 mmol, 2.5M in hexane) was gradually added thereto. The reaction mixture was stirred at −78° C. for one hour, and copper chloride (II) (1.48 g, 11 mmol) was added thereto at −78° C. The reaction solution was stirred for five hours, and washed with distilled water and ethylacetate at room temperature. The obtained ethylacetate layer was dried over $MgSO_4$ and then dried under a reduced pressure to obtain a crude product. The crude product was purified by silica gel column chromatography and recrystallized from dichloromethane and hexane to give intermediate H (622 mg, yield: 25%) and an intermediate I (746 mg, yield: 30%) as white solids. The structures of intermediates H and I were determined by $^1H$ NMR. Intermediate H: $^1H$ NMR ($CDCl_3$, 300 MHz) δ (ppm) 7.74 (d, 4H), 7.18 (d, 4H), 2.06 (s, 6H); $^{13}C$ NMR ($CDCl_3$, 100 MHz) δ (ppm) 142.8, 134.9, 134.5, 131.1, 126.4, 119.4, 19.9. Intermediate I: $^1H$ NMR ($CDCl_3$, 300 MHz) δ (ppm) 7.60 (s, 4H), 2.61 (s, 6H); $^{13}C$ NMR ($CDCl_3$, 100 MHz) δ (ppm) 138.3, 137.2, 129, 9, 125.8, 23.5.

Synthesis of Compound 18

Intermediate G (1.26 g, 4.4 mmol) and intermediate H (0.5 g, 1 mmol) were dissolved in THF (10 ml), and tetrakistrphenylphosphine palladium (92 mg, 0.08 mmol) and a solution of potassium carbonate (1.4 g, 10 mmol) in distilled water (10 ml) was sequentially added thereto. The reaction mixture was stirred at 75° C. for 12 hours. The reaction solution was extracted three times with ethylacetate (10 ml). The collected organic layer was dried over magnesium sulfate to evaporate a solvent. The resultant residue was purified by silica gel column chromatography to give compound 18 as a white solid (0.75 g, yield: 65%). The structure of compound 18 was determined by $^1H$ NMR. $^1H$ NMR ($CDCl_3$, 300 MHz) δ (ppm) 8.17 (d, 2H), 8.14 (s, 2H), 7.87 (d, 2H), 7.84 (d, 2H), 7.77 (d, 2H), 7.69 (s, 2H), 7.51-7.49 (m, 12H), 7.36-7.27 (m, 20H), 7.12 (dd, 2H), 7.04 (dd, 2H), 2.44 (s, 6H); $^{13}C$ NMR ($CDCl_3$, 100 MHz) δ (ppm) 157.3, 145.7, 144.7, 144.3, 140.1, 136.9, 136.1, 135.4, 131.8, 130.2, 129.8, 129.6, 129.1, 127.4, 127.1, 126.3, 124.5, 120.4, 119.9, 118.6, 118.3, 117.5, 117.2, 114.9, 114.2, 113.4, 109.1, 18.2.

Synthesis Example 4

Synthesis of Compound 20

Compound 20 was synthesized according to Reaction Scheme 4 below.

<Reaction Scheme 4>

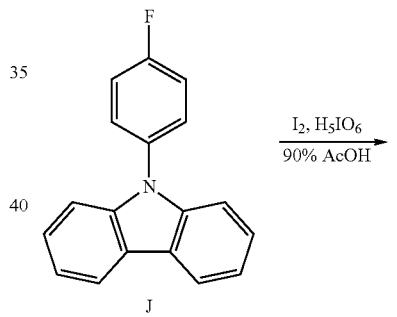

NMR (CDCl₃, 100 MHz) δ (ppm) 161.9, 155.4, 139.5, 136.8, 136.7, 126.2, 125.5, 125.3, 123.0, 123.4, 119.9, 113.8, 113.1, 109.6.

Synthesis of Intermediate K

Intermediate J (2.61 g, 10 mmol) was added to an 80% acetic acid (100 ml), and iodine (I₂) (1.357 g, 5.35 mmol) and ortho-periodinic acid (H₅IO₆) (0.333 g, 1.46 mmol) in a solid phase were added thereto. The reaction mixture was stirred at 80° C. under a nitrogen atmosphere for three hours. After the reaction was terminated, the reaction solution was extracted three times with ethylether (50 ml). The collected organic layer was dried over magnesium sulfate to evaporate a solvent. The resultant residue was purified by silica gel column chromatography to give intermediate K as a white solid (3.84 g, yield: 90%). The structure of intermediate K was determined by ¹H NMR. ¹H NMR (CDCl₃, 300 MHz) δ (ppm) 8.08 (d, 2H), 7.55-7.52 (m, 2H), 7.35-7.32 (m, 4H), 7.27-7.20 (m, 2H), 7.08-7.03 (m, 2H); ¹³C NMR (CDCl₃, 100 MHz) δ (ppm) 163.2, 158.3, 139.5, 136.8, 126.4, 125.5, 125.3, 123.0, 120.4, 119.9, 113.8, 113.1, 109.6.

Synthesis of Intermediate L

Intermediate K (3.13 g, 7.34 mmol) was added to THF (50 ml), and n-butyllithium (2.5M in hexane) (3.9 ml, 9.55 mmol) was dropwise added thereto at −78° C. The reaction mixture was stirred for one hour, and trimethylborate (2.5 ml, 22.0 mmol) was added thereto. The reaction solution was heated to room temperature, stirred for one hour, and hydrolyzed with a 2N HCl solution. The aqueous layer was extracted three times with ethylacetate (20 ml). The collected organic layer was dried over magnesium sulfate to evaporate a solvent. The resultant residue was purified by silica gel column chromatography to give intermediate L as a white solid (1.07 g, yield: 48%). The structure of intermediate L was determined by ¹H NMR. ¹H NMR (CDCl₃, 300 MHz) δ (ppm) 8.11 (s, 4H), 8.09 (s, 2H), 7.66 (d, 2H), 7.56-7.52 (m, 2H), 7.36-7.31 (m, 4H), 7.08-7.03 (m, 2H); ¹³C NMR (CDCl₃, 100 MHz) δ (ppm) 162.9, 158.1, 142.2, 139.3, 136.8, 136.6, 131.2, 130.6, 129.5, 128.4, 127.3, 126.3, 125.5, 125.3, 124.8, 119.2, 119.0, 113.8, 113.1, 109.6, 99.9, 95.3, 90.5.

Synthesis of Compound 20

Intermediate L (1.34 g, 4.4 mmol) and intermediate H (0.5 g, 1 mmol) were dissolved in THF (10 ml), and tetrakistriphenylphosphine palladium (92 mg, 0.08 mmol) and a solution of potassium carbonate (1.4 g, 10 mmol) in distilled water (10 ml) were sequentially added thereto. The reaction mixture was stirred at 75° C. for 12 hours. The reaction solution was extracted three times with ethylacetate (10 ml). The collected organic layer was dried over magnesium sulfate to evaporate a solvent. The resultant residue was purified by silica gel column chromatography to give compound 20 as a white solid (0.89 g, yield: 73%). The structure of compound 20 was determined by ¹H NMR. ¹H NMR (CDCl₃, 300 MHz) δ (ppm) 8.16 (d, 4H), 8.14 (s, 2H), 7.87 (d, 2H), 7.84 (d, 2H), 7.77 (d, 2H), 7.69 (d, 2H), 7.56-7.51 (m, 8H), 7.36-7.26 (m, 14H), 7.12 (dd, 2H), 7.09-7.02 (m, 10H), 2.46 (s, 6H); ¹³C NMR (CDCl₃, 100 MHz) δ (ppm) 163.2, 158.4, 155.5, 145.7, 144.3, 143.8, 143.7, 140.0, 136.1, 136.1, 136.0, 135.4, 131.8, -continued

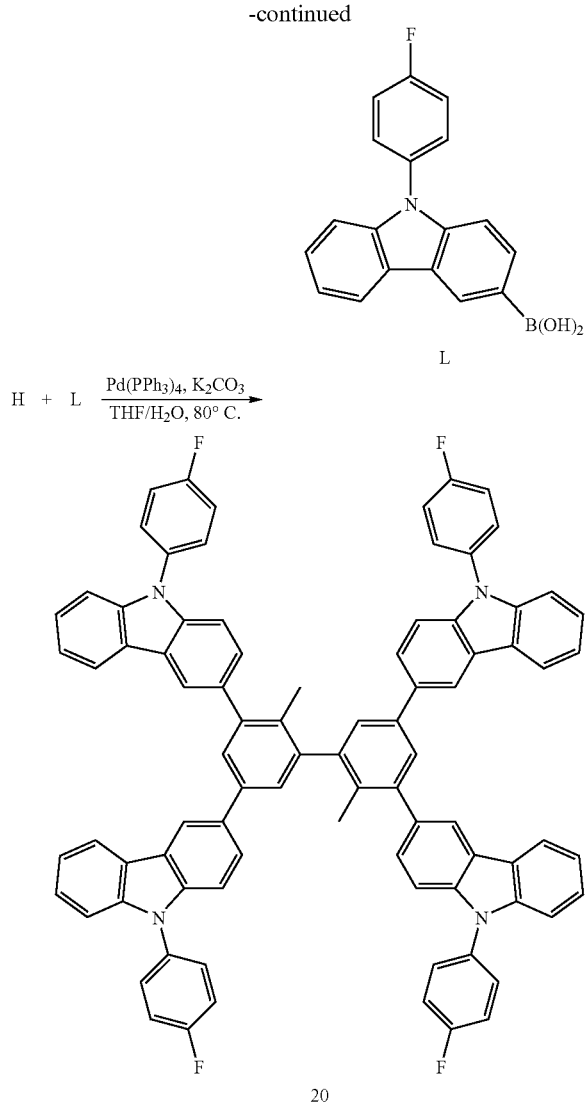

Synthesis of Intermediate J

Carbazole (16.7 g, 100 mmol), 4-fluoroiodobenzene (28.9 g, 130 mmol), CuI (1.9 g, 10 mmol), K₂CO₃ (138 g, 1.0 mol), and 18-crown-6 (530 mg, 2 mmol) were dissolved in DMPU (500 ml), and the reaction mixture was stirred at 170° C. for eight hours. After the reaction was terminated, the reaction solution was cooled to room temperature, and a solid material was filtered out. A trace amount of an ammonia solution was added to the filtrate, and the resultant solution was extracted three times with diethylether (300 ml). The collected diethylether layer was washed with excess distilled water, dried over MgSO₄, filtered, and dried under a reduced pressure to obtain a crude product. The crude product was purified by silica gel column chromatography to give intermediate J as a white solid (23.5 g, yield: 90%). The structure of intermediate J was determined by ¹H NMR. ¹H NMR (CDCl₃, 300 MHz) δ (ppm) 8.09 (d, 2H), 7.56-7.52 (m, 2H), 7.34 (d, 4H), 7.26-7.20 (m, 2H), 7.08-7.03 (m, 2H) 8.09 (d, 2H), 7.56-7.52 (m, 2H), 7.34 (d, 4H), 7.26-7.20 (m, 2H), 7.08-7.03 (m, 2H); ¹³C 130.1, 129.6, 129.1, 126.3, 125.5, 125.3, 124.5, 120.4, 119.9, 118.6, 118.3, 117.5, 117.1, 114.9, 114.2, 113.8, 113.4, 113.1, 108.9, 17.9.

Synthesis Example 5

Synthesis of Compound 23

Compound 23 was synthesized according to Reaction Scheme 5 below.

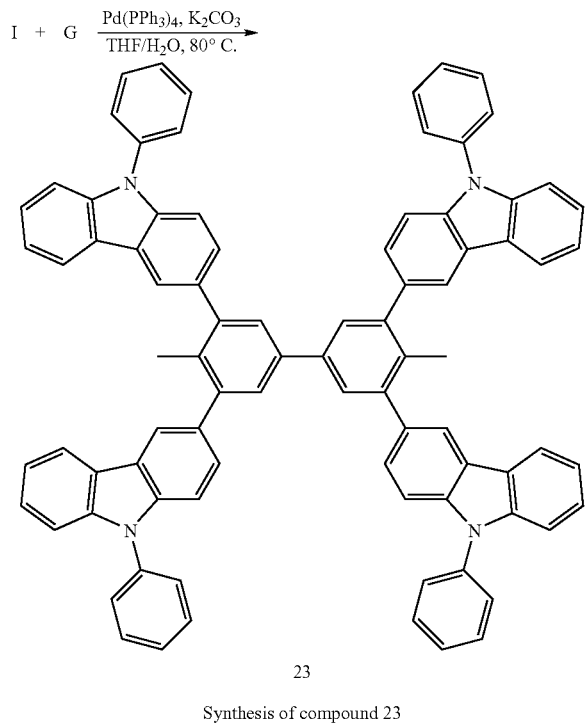

Synthesis of compound 23

Intermediate G (1.26 g, 4.4 mmol) and intermediate I (0.5 g, 1 mmol) were dissolved in THF (20 ml), and tetrakistriphenylphosphine palladium (92 mg, 0.08 mmol) and a solution of potassium carbonate (1.4 g, 10 mmol) in distilled water (10 ml) were sequentially added thereto. The reaction mixture was stirred at 75° C. for 12 hours. The reaction solution was extracted three times with ethylacetate (10 ml). The collected organic layer was dried over magnesium sulfate to evaporate a solvent. The resultant residue was purified by silica gel column chromatography to give compound 23 as a white solid (0.71 g, yield: 62%). The structure of compound 23 was determined by $^1$H NMR. $^1$H NMR (CDCl$_3$, 300 MHz) δ (ppm) 8.16 (d, 4H), 8.13 (s, 2H), 7.84 (d, 4H), 7.69 (s, 4H), 7.51-7.47 (m, 12H), 7.36-7.27 (m, 20H), 7.04 (dd, 4H), 2.63 (s, 6H); $^{13}$C NMR (CDCl$_3$, 100 MHz) δ (ppm) 146.6, 145.1, 144.7, 140.1, 137.0, 136.1, 132.1, 130.2, 129.8, 129.2, 127.4, 127.1, 126.3, 120.4, 119.9, 118.6, 117.5, 114.9, 113.5, 108.9, 23.2.

Example 1

A 15 Ω/cm$^2$ ITO glass substrate (Corning, 1,200 Å) was cut into pieces of 50 mm×50 mm×0.7 mm in size, followed by ultrasonic cleaning in isopropyl alcohol and pure water (5 minutes for each), exposure to UV light for 30 minutes, and then ozone cleaning, to thereby form anodes. The anodes were placed in a vacuum deposition machine.

Compound 1 according to the present invention was vacuum-deposited to a thickness of 600 Å on the anodes to form hole injection layers. Then, a hole transport compound, 4,4'-bis[N-(1-naphthyl)-N-phenylamino]biphenyl (NPB) was vacuum-deposited to a thickness of 300 Å on the hole injection layers to form hole transport layers.

A known blue fluorescent host, IDE215 (Idemitsu), and a known blue fluorescent dopant, IDE118 (Idemitsu) (weight ratio of 98:2) were co-deposited to a thickness of 200 Å on the hole transport layers to form emitting layers.

Next, Alq$_3$ was deposited to a thickness of 300 Å on the emitting layers to form electron transport layers. LiF (10 Å, electron injection layers), which is halogenated alkaline metal, and Al (3000 Å, cathodes) were vacuum-deposited on the electron transport layers to form LiF/Al electrodes, thereby completing organic light-emitting devices.

The organic light-emitting devices exhibited a driving voltage of 7.53 V at a current density of 100 mA/cm$^2$, a high brightness of 8,009 cd/m$^2$, color coordinates of (0.143, 0.238), and a high emission efficiency of 8.01 cd/A.

Example 2

Organic light-emitting devices were manufactured in the same manner as in Example 1 except that hole injection layers were formed using compound 13 instead of compound 1.

The organic light-emitting devices exhibited a driving voltage of 7.45 V at a current density of 100 mA/cm$^2$, a high brightness of 7,670 cd/m$^2$, color coordinates of (0.142, 0.240), and an emission efficiency of 7.67 cd/A.

Comparative Example 1

Organic light-emitting devices were manufactured in the same manner as in Example 1 except that hole injection layers were formed using IDE406 (Idemitsu) instead of compound 1.

The organic light-emitting devices exhibited a driving voltage of 7.75 V at a current density of 100 mA/cm$^2$, a brightness of 6,219 cd/m$^2$, color coordinates of (0.143, 0.243), and an emission efficiency of 6.22 cd/A.

When comparing the organic light-emitting devices employing the compounds of Formula 1 and the known IDE406, all the organic light-emitting devices employing the compounds of Formula 1 exhibited good I-V-L characteristics that were greater than or equal to those of the organic light-emitting devices employing IDE406. The organic light-emitting devices employing the compounds of Formula 1 also exhibited a low driving voltage, a high efficiency, and a high brightness, based on the good hole injection and transport capabilities of the compounds of Formula 1.

As described above, a carbazole-based compound of Formula 1 has good electrical characteristics and charge transport capability, and thus, is useful as a hole injection material, a hole transport material, and/or an emitting material for fluorescent or phosphorescent devices capable of producing light of a full spectrum of colors, including red, green, blue, and white. Thus, the carbazole-based compound can be used to produce an organic light-emitting device with high efficiency, a low driving voltage, and high brightness.

Although a few embodiments of the present invention have been shown and described, it would be appreciated by those skilled in the art that changes may be made in this embodi-

What is claimed is:

1. A carbazole-based compound represented by Formula 1 below:

<Formula 1>

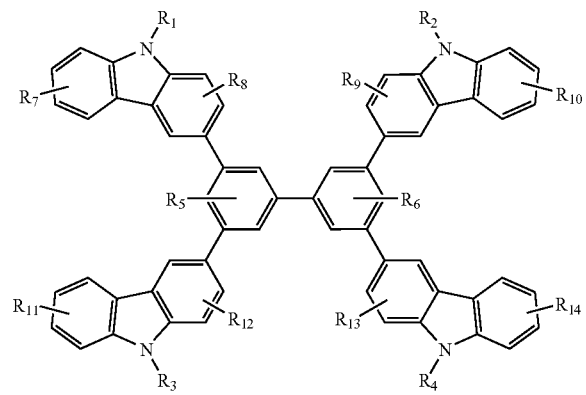

wherein, $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ are each independently hydrogen, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, or a substituted or unsubstituted $C_2$-$C_{30}$ heteroaryl group, and wherein adjacent groups selected from $R_1$, $R_2$, $R_3$, $R_4$, $R_5$, $R_6$, $R_7$, $R_8$, $R_9$, $R_{10}$, $R_{11}$, $R_{12}$, $R_{13}$, and $R_{14}$ may join together to form a saturated or unsaturated carbon ring.

2. The carbazole-based compound of claim 1, which is a compound selected from compounds represented by Formulae 2 through 4 below:

<Formula 2>

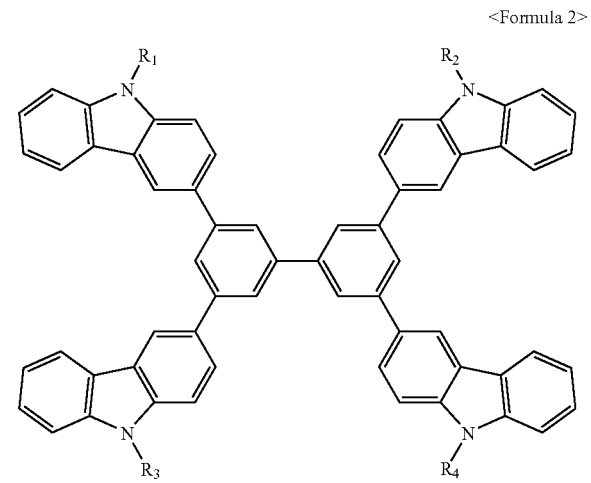

<Formula 3>

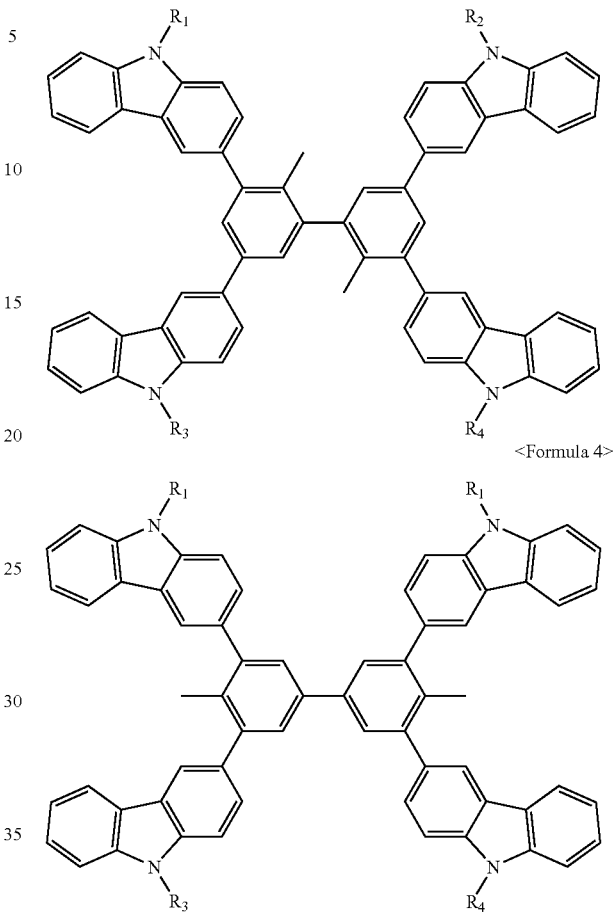

<Formula 4> wherein, $R_1$, $R_2$, $R_3$, and $R_4$ are each independently hydrogen, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, or a substituted or unsubstituted $C_2$-$C_{30}$ heteroaryl group.

3. The carbazole-based compound of claim 1, wherein $R_1$, $R_2$, $R_3$, and $R_4$ are each independently a substituted or unsubstituted $C_1$-$C_{10}$ alkyl group, a substituted or unsubstituted $C_1$-$C_{10}$ alkoxy group, a substituted or unsubstituted $C_6$-$C_{12}$ aryl group, a substituted or unsubstituted $C_6$-$C_{12}$ aryloxy group, or a substituted or unsubstituted $C_3$-$C_{12}$ heteroaryl group.

4. The carbazole-based compound of claim 1, wherein $R_1$, $R_2$, $R_3$, and $R_4$ are each independently a $C_1$-$C_{10}$ alkyl group, a phenyl group, a halophenyl group, a cyanophenyl group, a $C_1$-$C_{10}$ alkylphenyl group, a $C_1$-$C_{10}$ alkoxyphenyl group, a biphenyl group, a halobiphenyl group, a naphthyl group, a halonaphthyl group, a $C_1$-$C_{10}$ alkylnaphthyl group, or a $C_1$-$C_{10}$ alkoxynaphthyl group.

5. The carbazole-based compound of claim 1, which is selected from compounds 1-27 below:

-continued
1
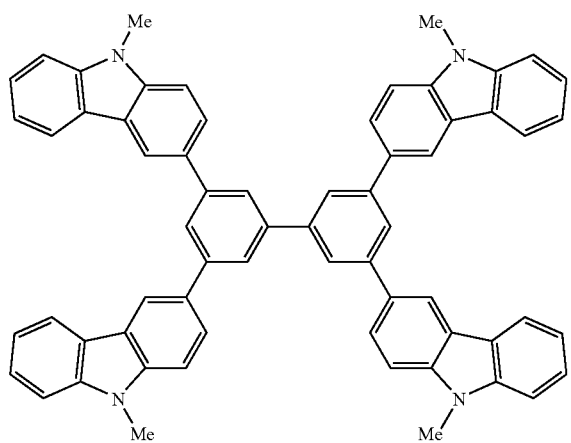
4
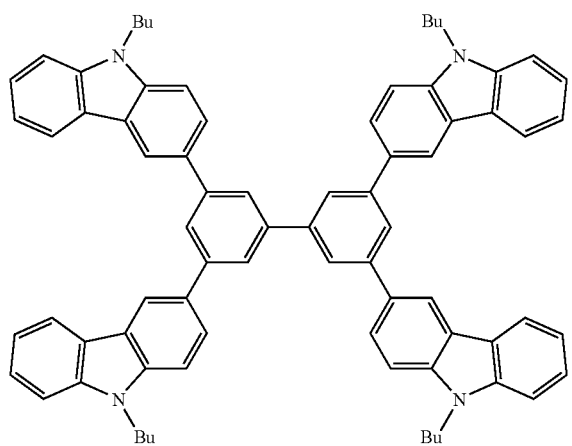
2
3
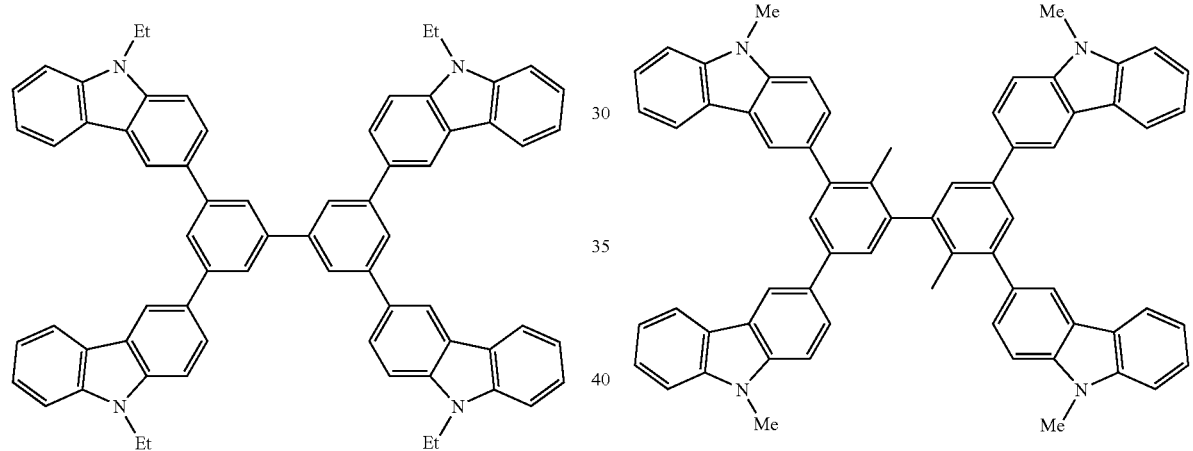
5
6
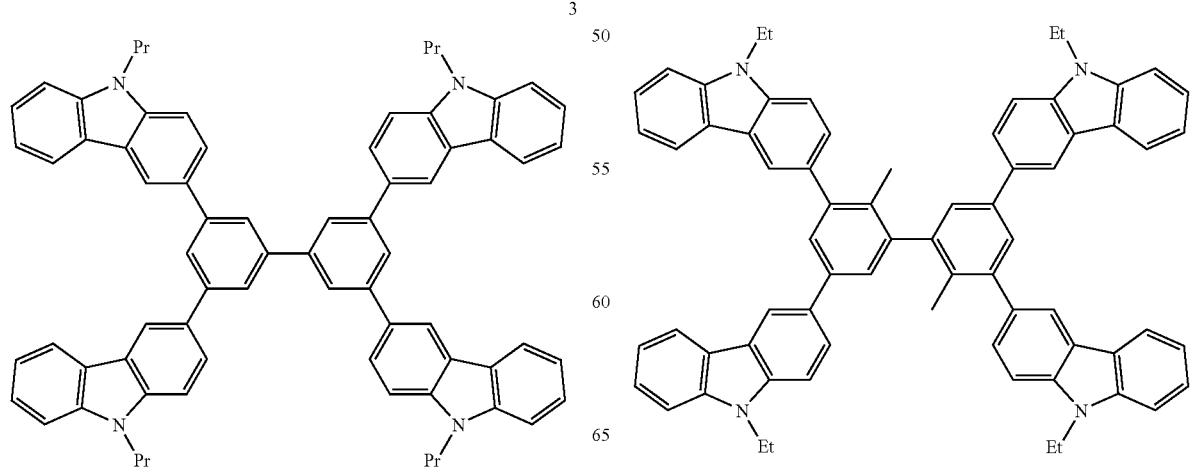

-continued
7
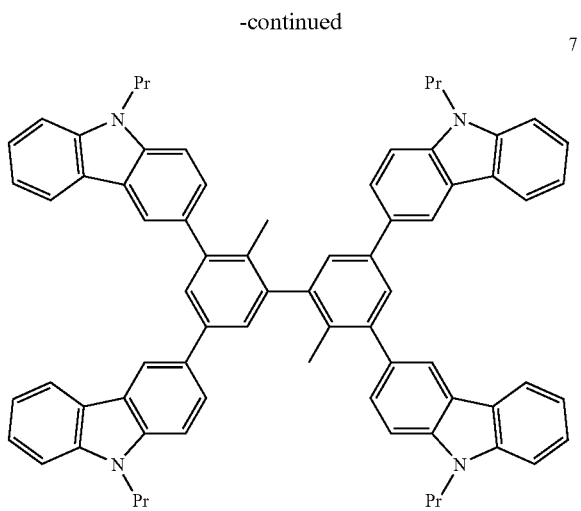
8
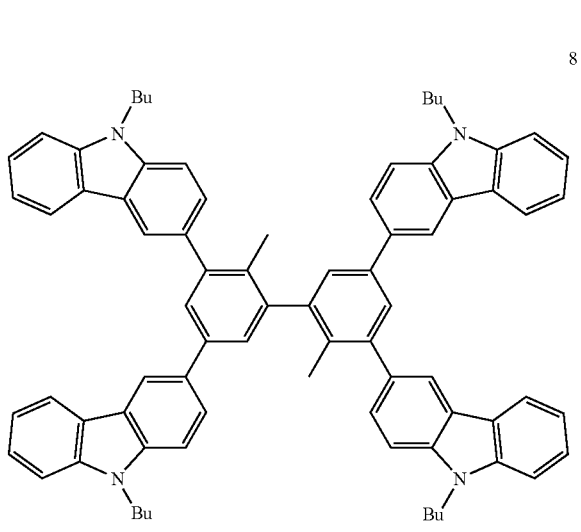
9
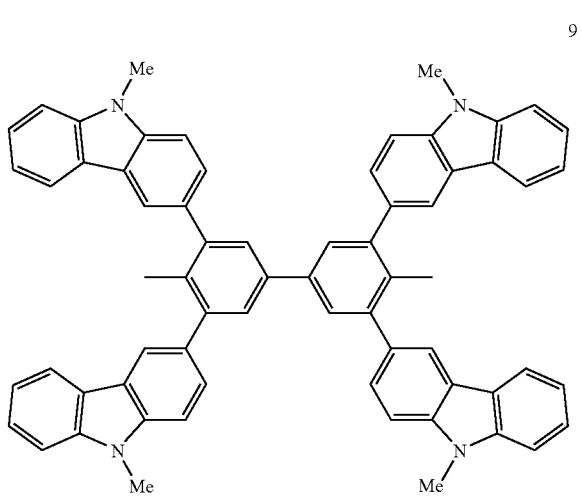
-continued
10
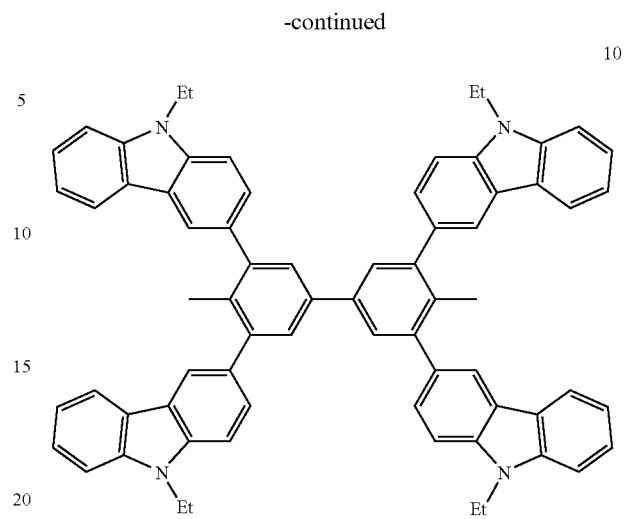
11
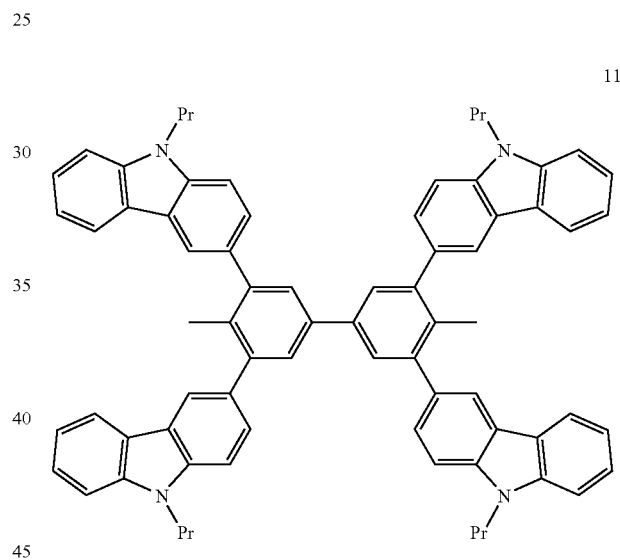
12
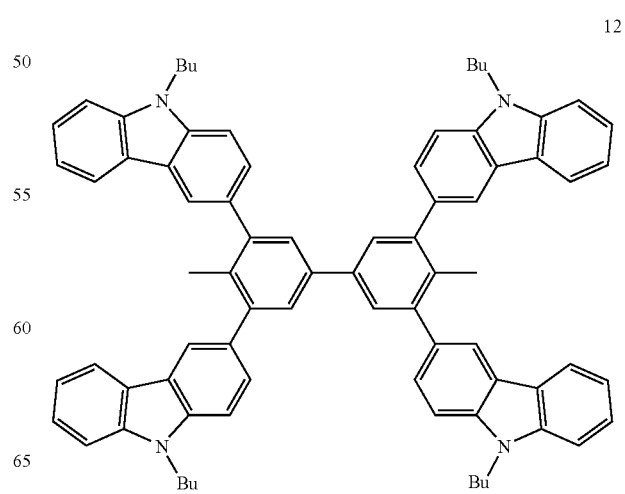

13
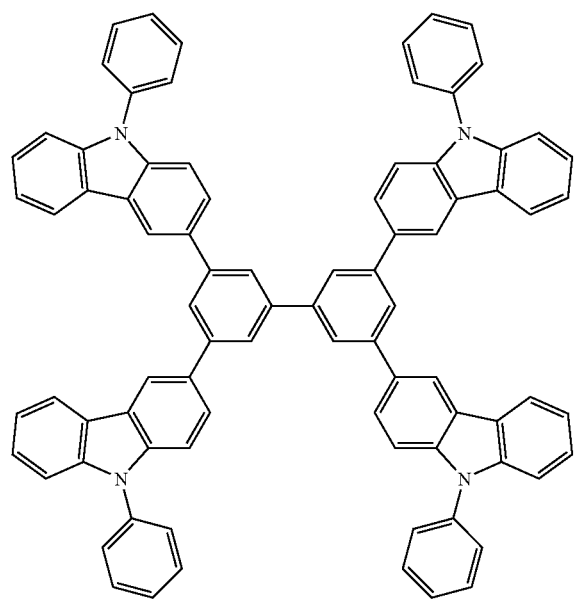
15
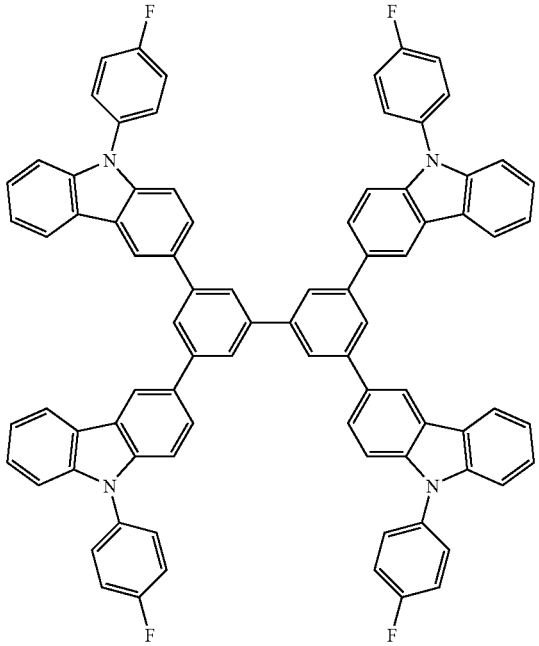
14
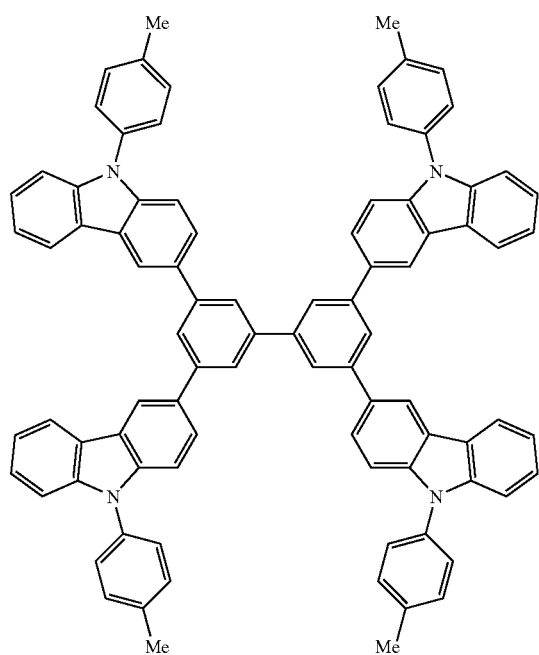
16
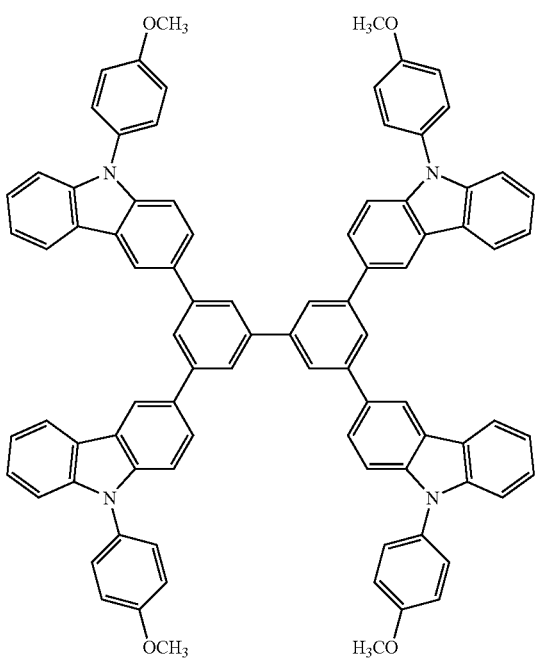

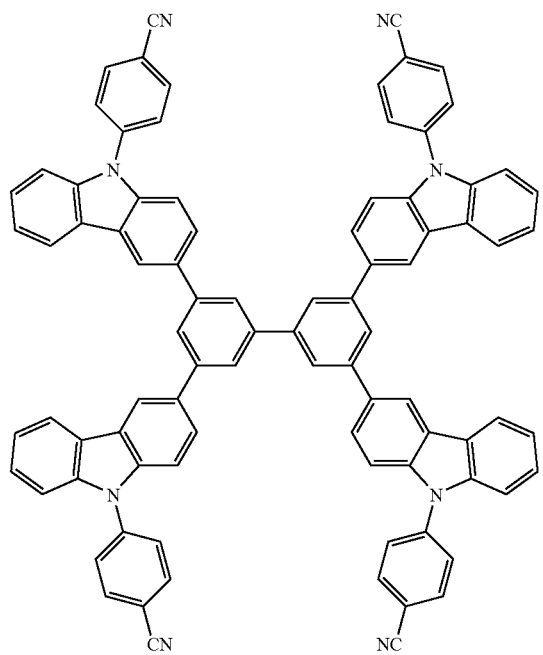
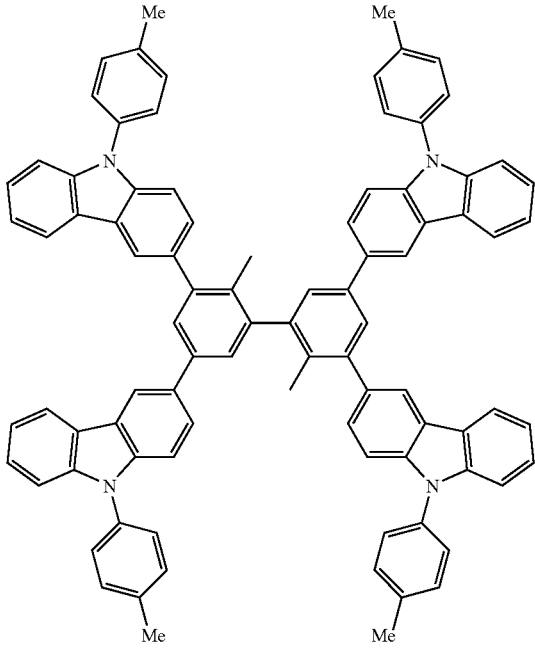
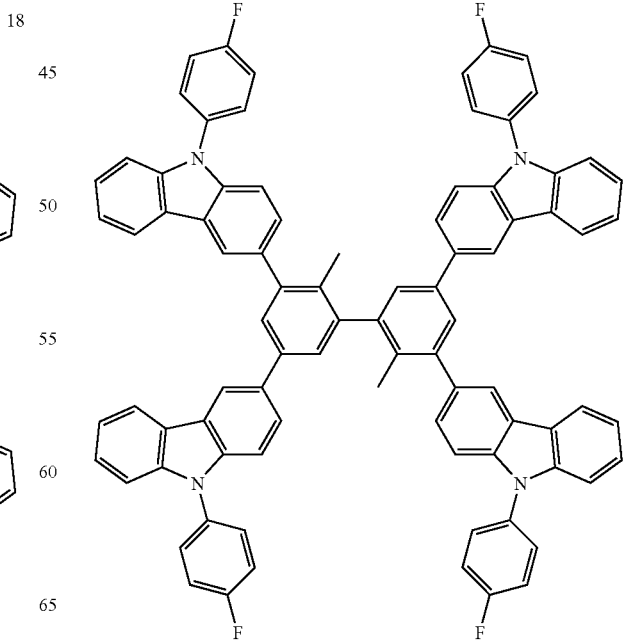

21
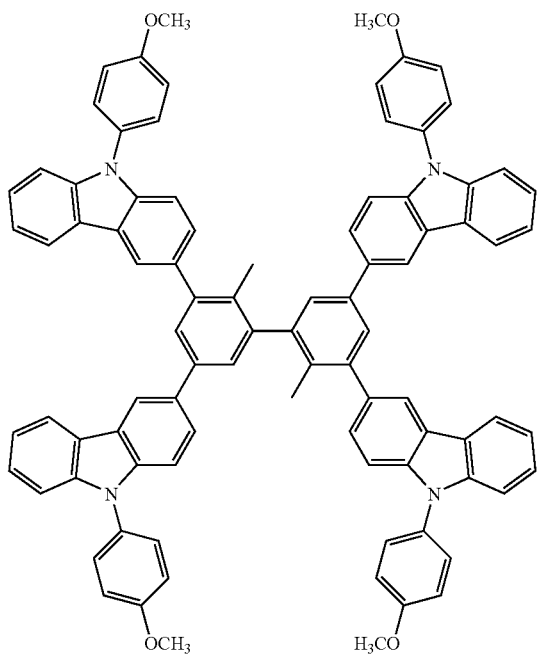
23
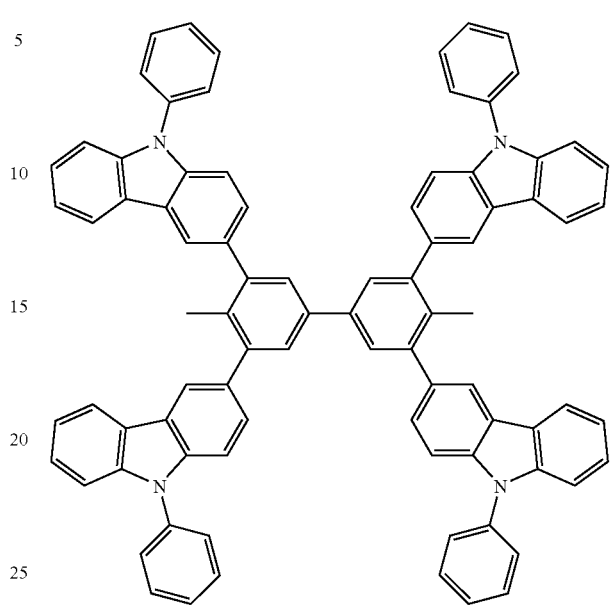
22
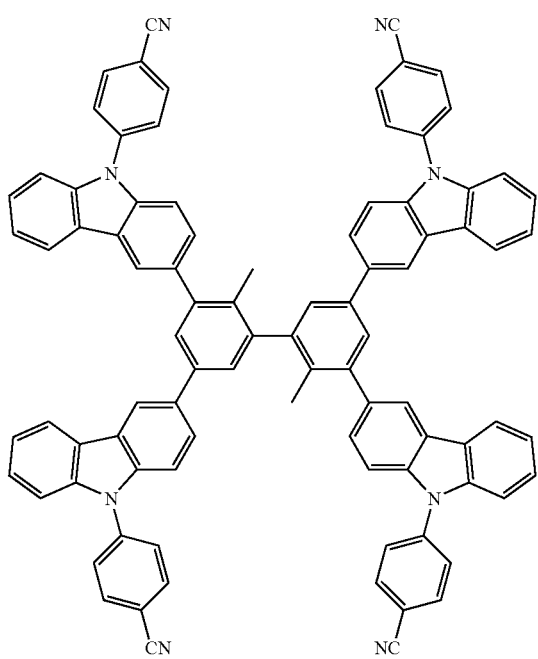
24
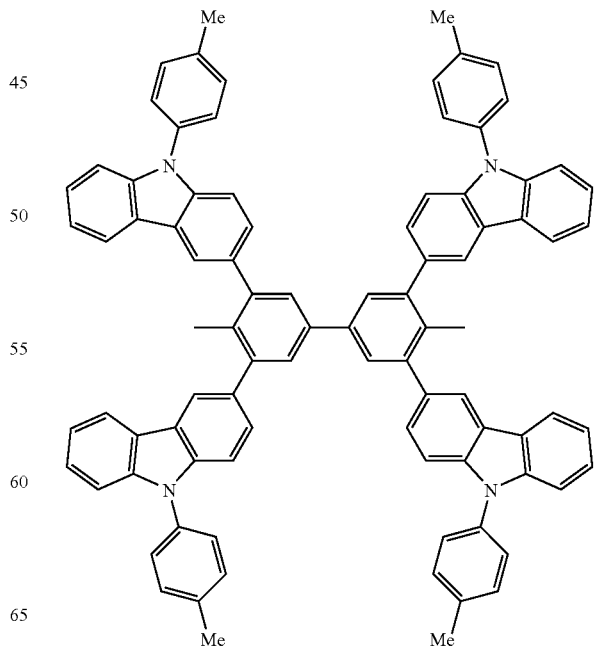

-continued

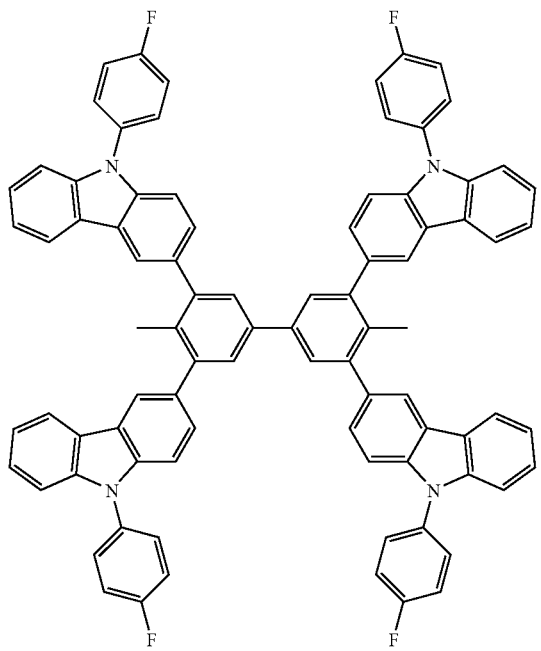
25

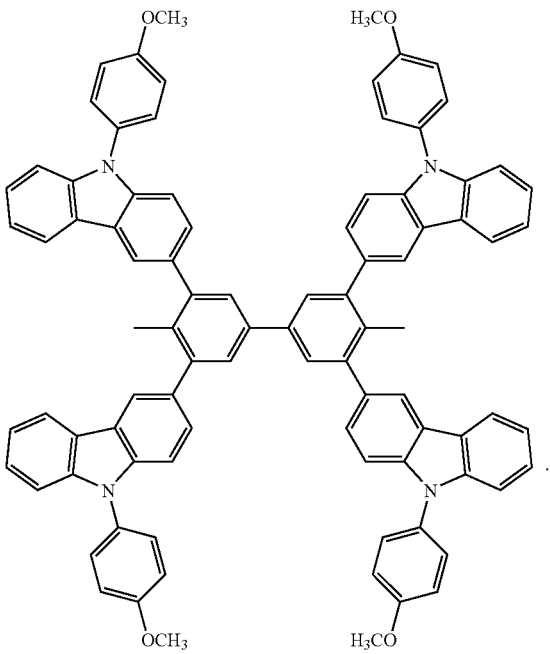
27

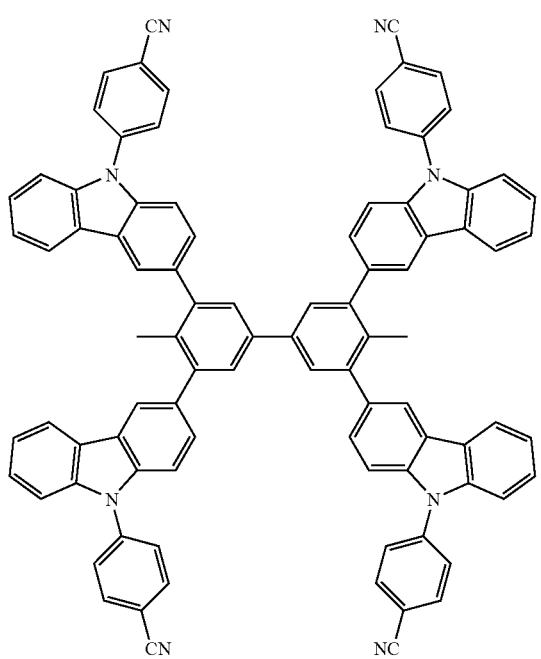
26

6. An organic light-emitting device comprising:
a first electrode;
a second electrode; and
one or more organic layers interposed between the first electrode and the second electrode, wherein at least one of the one or more organic layers comprises the carbazole-based compound of claim 1.

7. The organic light-emitting device of claim 6, wherein the organic layer comprising the carbazole-based compound is a hole injection layer or a hole transport layer.

8. The organic light-emitting device of claim 6, wherein the organic layer comprising the carbazole-based compound is a single layer having both a hole injection capability and a hole transport capability.

9. The organic light-emitting device of claim 7, which has one of the following structures:
first electrode/hole injection layer/emitting layer/second electrode;
first electrode/hole injection layer/hole transport layer/emitting layer/electron transport layer/second electrode; or
first electrode/hole injection layer/hole transport layer/emitting layer/electron transport layer/electron injection layer/second electrode.

10. The organic light-emitting device of claim 9, further comprising a hole blocking layer or an electron blocking layer or a hole blocking layer and an electron blocking layer.

11. The organic light-emitting device of claim 8, which has one of the following structures:
first electrode/single layer having hole injection capability and hole transport capability/emitting layer/electron transport layer/second electrode or
first electrode/single layer having hole injection capability and hole transport capability/emitting layer/electron transport layer/electron injection layer/second electrode.

12. The organic light-emitting device of claim 11, further comprising a hole blocking layer or an electron blocking layer or a hole blocking layer and an electron blocking layer.

13. The organic light-emitting device of claim 6, wherein the organic layer comprising the carbazole-based compound is an emitting layer.

14. The organic light-emitting device of claim 13, wherein the emitting layer comprises a phosphorescent or fluorescent material.

15. An organic light-emitting device comprising a hole injection layer or a hole transport layer or a single layer having both hole injection and hole transport capabilities comprising the carbazole-based compound of claim 1.

16. An organic light-emitting device comprising an emitting layer comprising the carbazole-based compound of claim 1.

* * * * *